(12) United States Patent
Mashima et al.

(10) Patent No.: US 7,888,513 B2
(45) Date of Patent: Feb. 15, 2011

(54) CONDENSATION REACTION BY METAL CATALYST

(75) Inventors: Kazushi Mashima, Suita (JP); Takashi Ohshima, Suita (JP); Takanori Iwasaki, Suita (JP); Hironori Maeda, Hiratsuka (JP); Kenya Ishida, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 346 days.

(21) Appl. No.: 12/085,988

(22) PCT Filed: Dec. 4, 2006

(86) PCT No.: PCT/JP2006/324176

§ 371 (c)(1),
(2), (4) Date: Jun. 4, 2008

(87) PCT Pub. No.: WO2007/066617

PCT Pub. Date: Jun. 14, 2007

(65) Prior Publication Data

US 2009/0198070 A1    Aug. 6, 2009

(30) Foreign Application Priority Data

Dec. 5, 2005   (JP)   ............... 2005-351163

(51) Int. Cl.
*C07F 15/00* (2006.01)
*C07D 263/08* (2006.01)
*C07D 263/52* (2006.01)

(52) U.S. Cl. ............ 548/101; 548/217; 548/237

(58) Field of Classification Search ............ None
See application file for complete search history.

(56) References Cited

FOREIGN PATENT DOCUMENTS

| DE | 3244956 | 6/1984 |
|----|---------|--------|
| JP | 3-197469 | 8/1991 |
| JP | 5-117254 | 5/1993 |
| JP | 9-87259 | 3/1997 |
| WO | 82/02046 | 6/1982 |
| WO | 88/04938 | 7/1988 |

OTHER PUBLICATIONS

Angew. Chem. Int. Ed. 2003, 42, No. 4, pp. 456-459.*
Zou et al., "Thermochemical process in preparation of ZnO film by TFA-MOD method," Applied Surface Science, vol. 253, pp. 4356-4360 (2007).
Joanne V. Allen, et al. "Enantiomerically Pure Oxazolines Teathered to Alcohols. Preparation and Use in Asymmetrical Catalysts." Tetrahedron: Asymmetry. 1994. vol. 5, No. 2, pp. 277-282.
Carsten Bolm, et al. "Synthesis of New Hydroxy Oxazolines and their use in the Catalytic Asymmetric Phenyl Transfer to Aldehydes." Tetrahedron: Asymmetry. 2005, vol. 16, pp. 1367-1376.
Fernando Garcia-Tellado, et al. "Solvent-Free Microwave-Assisted Efficient Synthesis of 4, 4-Disubstituted 2-Oxazolines." European Journal of Organic Chemistry. 2003, No. 22, pp. 4387-4391.

* cited by examiner

*Primary Examiner*—Kamal A Saeed
(74) *Attorney, Agent, or Firm*—Wenderoth, Lind & Ponack, L.L.P.

(57) ABSTRACT

The invention relates to a method for producing an azoline compound represented by the general formula (3):

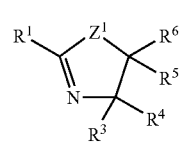

(3)

wherein $R^1$ represents an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; and $Z^1$ represents an oxygen atom, a sulfur atom or a selenium atom;

comprising reacting a carboxylic acid or a carboxylic acid derivative represented by the general formula (1):

$$R^1CO_2R^2 \qquad (1)$$

wherein $R^1$ is as defined above; $R^2$ represents a hydrogen atom, an optionally substituted alkyl group or an optionally substituted aryl group; and $R^1$ and $R^2$ may bond to each other to form a ring;

with an aminochalcogenide represented by the general formula (2):

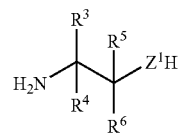

(2)

wherein $R^3$, $R^4$, $R^5$, $R^6$ and $Z^1$ are as defined above;
in the presence of a compound containing a group 12 metal element in the periodic table.

9 Claims, No Drawings

CONDENSATION REACTION BY METAL CATALYST

This application is a U.S. national stage of International Application No. PCT/JP2006/324176 filed Dec. 4, 2006.

TECHNICAL FIELD

The present invention relates to a method for producing an oxazoline compound, a thiazoline compound or a selenazoline compound (hereinafter, these compounds are collectively referred to as azoline compound) by cyclization reaction of an aminoalcohol, an aminothiol or an aminoselenol (hereinafter, these compounds are collectively referred to aminochalcogenides) with a carboxylic acid, or a carboxylate or a nitrile in the presence of a metal catalyst containing a group 12 metal element in the periodic table. The present invention also relates to a method for producing an amide compound by condensation reaction of a primary amine with a carboxylic acid or a carboxylate by the metal catalyst. Further, the present invention relates to a method for producing peptides by polycondensation of amino acids by the metal catalyst.

The azoline compounds obtained in the present invention are useful compounds as various intermediate raw materials, metal ligands, and the like. The amide compounds or the peptides obtained in the present invention are useful as pharmaceutical intermediates or functional materials and intermediates thereof.

The production method according to the present invention can be used to produce an optically active azoline compound and optically active peptides by using an optically active substance as aminochalcogenide and amino acids which are starting materials.

BACKGROUND ART

As a method for producing azoline compounds, particularly for example oxazoline compounds, a method for cyclodehydration by heating an amidoalcohol in the presence of a catalyst is known, and various catalysts have been proposed. As the catalysts, for example a tin alkanoate has been used in JP-A 60-246378, an iron salt has been used in JP-A 56-128772, and an organic acid salt of zinc has been used in U.S. Pat. No. 4,354,029.

In these methods using an amidoalcohol, however, a substituent at the 2-position of oxazoline compound as a product is determined depending on the type of an acyl group on the amino group of amidoalcohol as a starting material, so there is a problem that it is difficult to produce various oxazoline compounds.

A method of reacting an alkanol amine with nitrile in the presence of zinc acetate as a catalyst has been proposed in JP-A 59-21674. In this method, however, there is a problem that the yield is low unless the reaction temperature is high (about 190° C.).

Synlett, 2005, 15, 2321 has been described a method for producing a bisoxazoline compound from a dinitrile and an amino alcohol using zinc trifluoromethanesulfonate. JP-A 2002-275166 has been described a method for producing a cyclic imino ether (oxazoline compound) from a nitrile and an amino alcohol by using basic zinc acetate as a catalyst. However, nitrile as a starting material may be hardly obtained, and therefore, a method using a carboxylic acid or a carboxylate which is more easily obtainable than a nitrile in place of nitrile has been also examined.

For example, Org. Lett., 2002, 4, 3399 has been described a method for producing an oxazoline compound from a carboxylic acid and an amino alcohol by using stoichiometric quantities of triphenyl phosphine/carbon tetrachloride. J. Comb. Chem., 2002, 4, 656 has been described a method for producing an oxazoline compound from a carboxylic acid and an amino alcohol by using 3-nitrophenylboronic acid as a catalyst.

As for a method using a carboxylate as a starting material, Tetrahedron Lett., 1997, 38, 7019, for example, has been described a method for producing an oxazoline compound by using an equivalent amount of n-butyl lithium and a catalytic amount of a lanthanoid compound such as samarium chloride. Further, Tetrahedron Lett., 1990, 31, 6005 has been described a method for producing oxazolines by using dimethyltin chloride as a catalyst after dehydration reaction of diethyl malonate and an amino alcohol.

As a method for producing an amide compound and peptides, various production methods have been known, and examples of such methods include a method comprising the steps of heating a carboxylic acid or a carboxylate and amines and removing the formed water or alcohol out of the system, a method of using a condensation agent such as dicyclohexyl carbodiimide, and a method of using a Lewis acid (see Synlett, 2005, 15, 2321). In these methods, however, there are problems that, for example, heating at high temperature and an excess of a condensation agent are required.

DISCLOSURE OF THE INVENTION

Problems to be Solved by the Invention

An object of the present invention is to solve the problems described above, and to provide a novel method for producing an azoline compound highly selectively and efficiently from an aminochalcogenide and a carboxylic acid, a carboxylate or nitriles. Another object of the present invention is to provide a novel method for producing amides efficiently from primary amines and a carboxylic acid or a carboxylate, as well as a novel method for producing peptides efficiently from amino acids.

Means for Solving the Problems

The present inventors made extensive study for the objects described above, and as a result, they have found that in the presence of a compound of the group 12 metal in the periodic table, an azoline compound can be produced highly selectively by cyclization reaction of an aminochalcogenide with a carboxylic acid or a carboxylate, that amides can be obtained by reacting a primary amine with a carboxylic acid or a carboxylate, and that peptides can be obtained by polycondensation of amino acids, and the present invention has been thereby completed.

That is, the present invention encompasses the following (1) to (12):

(1) A method for producing an azoline compound represented by the general formula (3):

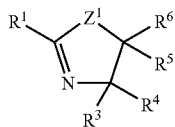
(3)

wherein $R^1$ represents an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; and $Z^1$ represents an oxygen atom, a sulfur atom or a selenium atom;

comprising reacting a carboxylic acid or a carboxylic acid derivative represented by the general formula (1):

$$R^1CO_2R^2 \quad (1)$$

wherein $R^1$ is as defined above; $R^2$ represents a hydrogen atom, an optionally substituted alkyl group or an optionally substituted aryl group; and $R^1$ and $R^2$ may bond to each other to form a ring;

with an aminochalcogenide represented by the general formula (2):

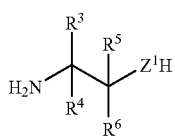
(2)

wherein $R^3$, $R^4$, $R^5$, $R^6$ and $Z^1$ are as defined above; in the presence of a compound containing a group 12 metal element in the periodic table.

(2) The method according to the above-mentioned (1), wherein the compound containing a group 12 metal element in the periodic table is a zinc compound.

(3) The method according to the above-mentioned (2), wherein the zinc compound is a compound represented by the general formula (4):

$$Zn_a(OCOR^7)_bZ^2_c \quad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when a is 1, b is 2 and c is 0, and when a is 4, b is 6 and c is 1.

(4) A method for producing a bisazoline compound represented by the general formula (9):

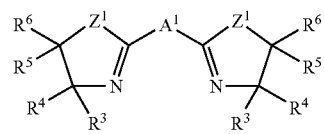
(9)

wherein $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; $Z^1$ represents an oxygen atom, a sulfur atom or a selenium atom; and $A^1$ represents a single bond, a divalent hydrocarbon group or a divalent heterocyclic group;

comprising reacting a compound represented by the general formula (8):

$$R^2OCO\text{-}A^1\text{-}CO_2R^2 \quad (8)$$

wherein $R^2$ represents a hydrogen atom, an optionally substituted alkyl group or an optionally substituted aryl group; and $A^1$ is as defined above;

with an aminochalcogenide represented by the general formula (2):

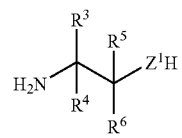
(2)

wherein $R^3$, $R^4$, $R^5$, $R^6$ and $Z^1$ are as defined above;

in the presence of a zinc compound represented by the general formula (4):

$$Zn_a(OCOR^7)_bZ^2_c \quad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when a is 1, b is 2 and c is 0, and when a is 4, b is 6 and c is 1.

(5) A method for producing an azoline compound represented by the general formula (5):

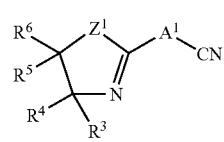
(5)

wherein $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; $A^1$ represents a single bond, a divalent hydrocarbon group or a divalent heterocyclic group; and $Z^1$ represents an oxygen atom, a sulfur atom or a selenium atom;

comprising reacting cyanocarboxylic acids represented by the general formula (8-2):

$$NC\text{-}A^1\text{-}CO_2R^2 \qquad (8\text{-}2)$$

wherein $R^2$ represents a hydrogen atom, an optionally substituted alkyl group or an optionally substituted aryl group; and $A^1$ is as defined above;

with an aminochalcogenide represented by the general formula (2):

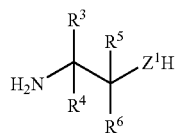

$$(2)$$

wherein $R^3$, $R^4$, $R^5$, $R^6$ and $Z^1$ are as defined above; in the presence of a zinc compound represented by the general formula (4):

$$Zn_a(OCOR^7)_b Z^2_c \qquad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when "a" is 1, "b" is 2 and "c" is 0, and when "a" is 4, "b" is 6 and "c" is 1.

(6) A method for producing an unsymmetrical bisazoline compound represented by the general formula (9-2):

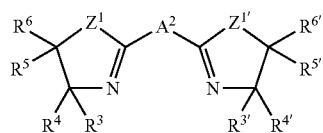

$$(9\text{-}2)$$

wherein $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; $R^{3'}$, $R^{4'}$, $R^{5'}$ and $R^{6'}$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^{3'}$, $R^{4'}$, $R^{5'}$ and $R^{6'}$ may bond to each other to form a ring; $A^2$ represents a single bond, a divalent hydrocarbon group or a divalent heterocyclic group; $Z^1$ represents an oxygen atom, a sulfur atom or a selenium atom; and $Z^{1'}$ represents an oxygen atom, a sulfur atom or a selenium atom;

comprising reacting a compound represented by the general formula (8-3):

$$R^2OCO\text{-}A^2\text{-}X^1 \qquad (8\text{-}3)$$

wherein $R^2$ represents a hydrogen atom, an optionally substituted alkyl group or an optionally substituted aryl group; $A^2$ is as defined above; and $X^1$ represents a cyano group or a carboxyl group;

with an aminochalcogenide represented by the general formula (2):

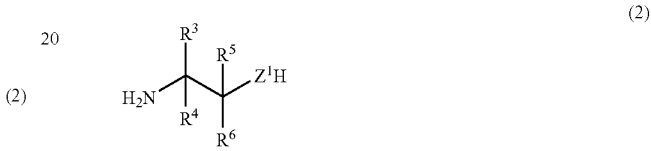

$$(2)$$

wherein $R^3$, $R^4$, $R^5$, $R^6$ and $Z^1$ are as defined above; in the presence of a zinc compound represented by the general formula (4):

$$Zn_a(OCOR^7)_b Z^2_c \qquad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when "a" is 1, "b" is 2 and "c" is 0, and when "a" is 4, "b" is 6 and "c" is 1; and reacting the reaction product with an aminochalcogenide represented by the general formula (2-2):

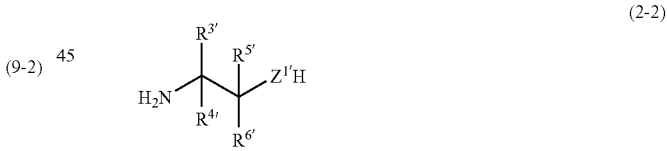

$$(2\text{-}2)$$

wherein $R^{3'}$, $R^{4'}$, $R^{5'}$, $R^{6'}$ and $Z^{1'}$ are as defined above.

(7) A method for producing amides represented by the general formula (7):

$$R^1CONHR^8 \qquad (7)$$

wherein $R^1$ represents an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; and $R^8$ represents an optionally substituted hydrocarbon group;

comprising reacting a carboxylic acid or a carboxylic acid derivative represented by the general formula (1):

$$R^1CO_2R^2 \qquad (1)$$

wherein $R^1$ is as defined above; $R^2$ represents a hydrogen atom, an optionally substituted alkyl group or an optionally substituted aryl group; and $R^1$ and $R^2$ may bond to each other to form a ring;

with amines represented by the general formula (6):

$$R^8NH_2 \qquad (6)$$

wherein $R^8$ is as defined above;

in the presence of a zinc compound represented by the general formula (4):

$$Zn_a(OCOR^7)_bZ^2_c \qquad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when "a" is 1, "b" is 2 and "c" is 0, and when "a" is 4, "b" is 6 and "c" is 1.

(8) A method for producing bisamides represented by the general formula (7-2):

$$R^8NHCO\text{-}A^3\text{-}CONHR^8 \qquad (7\text{-}2)$$

wherein $R^8$ represents an optionally substituted hydrocarbon group; and $A^3$ represents a single bond, a divalent hydrocarbon group or a divalent heterocyclic group;

comprising reacting a dicarboxylic acid represented by the general formula (8-4):

$$R^2OCO\text{-}A^3\text{-}CO_2R^{2'} \qquad (8\text{-}4)$$

wherein $R^2$ and $R^{2'}$ may be the same or different and each represents a hydrogen atom, an optionally substituted alkyl group or an optionally substituted aryl group; and $A^3$ is as defined above; with amines represented by the general formula (6):

$$R^8NH_2 \qquad (6)$$

wherein $R^8$ is as defined above;

in the presence of a zinc compound represented by the general formula (4):

$$Zn_a(OCOR^7)_bZ^2_c \qquad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when "a" is 1, "b" is 2 and "c" is 0, and when "a" is 4, "b" is 6 and "c" is 1.

(9) A method for producing cyanoamides represented by the general formula (7-3):

$$R^8NHCO\text{-}A^2\text{-}CN \qquad (7\text{-}3)$$

wherein $R^8$ represents an optionally substituted hydrocarbon group; and $A^2$ represents a single bond, a divalent hydrocarbon group or a divalent heterocyclic group;

comprising reacting cyanocarboxylic acids represented by the general formula (8-2):

$$NC\text{-}A^2\text{-}CO_2R^2 \qquad (8\text{-}2)$$

wherein $R^2$ represents a hydrogen atom, an optionally substituted alkyl group or an optionally substituted aryl group; and $A^2$ is as defined above;

with amines represented by the general formula (6):

$$R^8NH_2 \qquad (6)$$

wherein $R^8$ is as defined above;

in the presence of a zinc compound represented by the general formula (4):

$$Zn_a(OCOR^7)_bZ^2_c \qquad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when "a" is 1, "b" is 2 and "c" is 0, and when "a" is 4, "b" is 6 and "c" is 1.

(10) A method for producing peptides represented by the general formula (11):

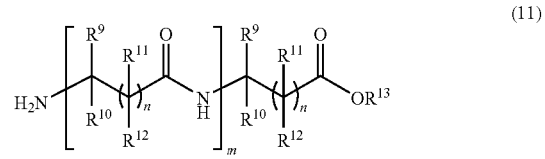

$$(11)$$

wherein $R^9$, $R^{10}$, $R^{11}$ and $R^{12}$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; a plurality of $R^9$s, $R^{10}$s, $R^{11}$s or $R^{12}$s may be the same or different; $R^{13}$ represents a hydrogen atom, an optionally substituted alkyl group or an optionally substituted aryl group; n represents an integer; and "m" represents an integer of 1 or more;

comprising subjecting same or different amino acids represented by represented by the general formula (10) to intermolecular condensation with one another:

$$(10)$$

wherein $R^9$, $R^{10}$, $R^{11}$ and $R^{12}$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; and $R^{13}$ and n are as defined above;

in the presence of a zinc compound represented by the general formula (4):

$$Zn_a(OCOR^7)_bZ^2_c \qquad (4)$$

wherein $R^7$ represents an optionally substituted alkyl group or an optionally substituted aryl group; $Z^2$ represents an oxygen atom, a sulfur atom or a selenium atom; "a" represents 1 or 4, "b" represents 2 or 6, and "c" represents 0 or 1; and provided that when "a" is 1, "b" is 2 and "c" is 0, and when "a" is 4, "b" is 6 and "c" is 1.

(11) A zinc compound represented by the formula (12).

$$Zn_4(OCOCF_3)_6O \quad (12)$$

(12) An azoline compound represented by the general formula (13):

(13)

wherein $R^{14}$ represents an alkyl group having 4 to 20 carbon atoms, an optionally substituted phenyl group, a hydroxyalkyl group having 2 to 6 carbon atoms, or a phenylalkyl group whose alkyl moiety has 2 to 10 carbon atoms; $R^{15}$ represents an alkyl group having 2 to 6 carbon atoms, an optionally substituted phenyl group, or a phenylalkyl group whose alkyl moiety has 1 to 6 carbon atom(s); $R^{16}$ and $R^{17}$ may be the same or different and each represents a hydrogen atom or an alkyl group having 1 to 6 carbon atom(s); and $R^{15}$, together with $R^{16}$ or $R^{17}$, may form a ring.

Effects of the Invention

According to the present invention, there can be provided a method for producing an azoline compound highly selectively and efficiently from an aminochalcogenide and a carboxylic acid, a carboxylate or nitriles, and there can be further provided a method for producing amides efficiently from primary amines and a carboxylic acid or a carboxylate and a method for producing peptides efficiently by condensation of amino acids. The azolines obtained in the present invention are useful as a ligand of a metal complex, a pharmaceutical intermediate or the like, and amides and peptides are useful as intermediates of various compounds or the like.

BEST MODE FOR CARRYING OUT THE INVENTION

Hereinafter, the present invention will be described in detail.

The aminochalcogenide in the production method of the present invention refers to aminoalcohols, aminothiols and aminoselenols. The azoline compound in the production method of the present invention refers to an oxazoline compound, a thiazoline compound and a selenazoline compound.

The hydrocarbon group represented by $R^1$, $R^3$, $R^4$, $R^5$, $R^6$, $R^{3'}$, $R^{4'}$, $R^{5'}$, $R^{6'}$, $R^8$, $R^9$, $R^{10}$, $R^{11}$ or $R^{12}$ in the objective compounds represented by the general formulae (1) to (11) and in the compounds used in the respective reactions is not particularly limited, and examples include an alkyl group, an alkenyl group, an alkynyl group and an aryl group and the like.

The alkyl group includes alkyl groups which may be linear, branched or cyclic. These alkyl groups are for example those having 1 to 20 carbon group(s), preferably 1 to 10 carbon atom(s), more preferably 1 to 6 carbon atom(s), and specific examples include, but not limited to, linear or branched alkyl groups such as a methyl group, an ethyl group, an n-propyl group, an isopropyl group, an n-butyl group, a sec-butyl group, an isobutyl group, a tert-butyl group, an n-pentyl group, a neopentyl group, a tert-pentyl group, a hexyl group, a heptyl group, an octyl group, a nonyl group, a decyl group, a cetyl group and a stearyl group; and cycloalkyl groups such as a cyclopentyl group, a methylcyclopentyl group, a cyclohexyl group, a methylcyclohexyl group and a cyclooctyl group and the like.

The alkenyl group includes, but not limited to, alkenyl groups which may be linear or branched, and specific examples include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 1-cyclohexenyl group and a 3-cyclohexenyl group and the like.

The alkynyl group includes, but not limited to, alkynyl groups which may be linear or branched, and specific examples include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group and a 5-hexynyl group and the like.

The aryl group includes, but not limited to, aryl groups having 6 to 20 carbon atoms, and specific examples include a phenyl group, a naphthyl group, an anthryl group, a phenanthryl group, a biphenyl group and a terphenyl group and the like.

Substituents which may be substituted on these hydrocarbon groups include a hydrocarbon group, a heterocyclic group, an alkoxy group, an alkylenedioxy group, an aryloxy group, an aralkyloxy group, a heteroaryloxy group, an alkylthio group, an arylthio group, an aralkylthio group, a heteroarylthio group, a substituted amino group, a nitro group, a tri-substituted silyloxy group and a halogen atom.

The hydrocarbon group as a substituent on the hydrocarbon groups includes, for example, an alkyl group, an alkenyl group, an alkynyl group, an aryl group and an aralkyl group.

The alkyl group as a substituent on the alkyl groups may be linear, branched or cyclic, preferably having for example 1 to 20 carbon atom(s), and examples include, but not limited to, linear or branched alkyl groups such as a methyl group, an ethyl group, an n-propyl group, an isopropyl group, an n-butyl group, a sec-butyl group, an isobutyl group, a tert-butyl group, an n-pentyl group, a neopentyl group, a tert-pentyl group, a hexyl group, a heptyl group, an octyl group, a nonyl group, a decyl group, a cetyl group and a stearyl group; and cycloalkyl groups such as a cyclopentyl group, a cyclohexyl group and a cyclooctyl group and the like.

The alkenyl group as a substituent on the hydrocarbon groups may be linear or branched, having for example 2 to 15 carbon atoms, preferably 2 to 10 carbon atoms, more preferably 2 to 6 carbon atoms. Specific examples include a vinyl group, a 1-propenyl group, an allyl group, a 1-butenyl group, a pentenyl group and a hexenyl group and the like.

The alkynyl group as a substituent on the hydrocarbon groups may be linear or branched, having for example 2 to 15 carbon groups, preferably 2 to 10 carbon atoms, more preferably 2 to 6 carbon atoms. Specific examples include an ethynyl group, a 1-propynyl group, a 2-propynyl group, a 1-butynyl group, a 3-butynyl group, a pentynyl group and a hexynyl group and the like.

The aryl group as a substituent on the hydrocarbon groups includes, for example, aryl groups having 6 to 20 carbon atoms, and specific examples include a phenyl group, a naphthyl group, an anthryl group, a phenanthryl group, a biphenyl group and a terphenyl group and the like.

The aralkyl group as a substituent on the hydrocarbon groups includes an alkyl group in which at least one hydrogen atom in the above alkyl group is substituted with the above aryl group, and is preferably an aralkyl group having for example 7 to 12 carbon atoms. Specific examples include a benzyl group, a 2-phenylethyl group, a 1-phenylpropyl group and a 3-naphthylpropyl group and the like.

The heterocyclic group as a substituent on the hydrocarbon groups includes an aliphatic heterocyclic group and an aromatic heterocyclic group. The aliphatic heterocyclic group includes 5- to 8-membered, preferably 5- or 6-membered monocyclic aliphatic heterocyclic groups or polycyclic or condensed-ring aliphatic heterocyclic groups, for example having 2 to 14 carbon atoms and containing at least 1, preferably 1 to 3 heteroatoms such as a nitrogen atom, an oxygen atom and a sulfur atom. Specific examples of the aliphatic heterocyclic group include a piperidino group, a piperazinyl group, a morpholino group, a tetrahydrofuryl group, a tetrahydropyranyl group and a tetrahydrothienyl group and the like.

The aromatic heterocyclic group as a substituent on the hydrocarbon groups includes, for example, 5- to 8-membered, preferably 5- or 6-membered monocyclic heteroaryl groups or polycyclic or condensed-ring heteroaryl groups, for example having 2 to 15 carbon atoms and containing at least 1, preferably 1 to 3 heteroatoms such as a nitrogen atom, an oxygen atom and a sulfur atom. Specific examples include a furyl group, a thienyl group, a pyridyl group, a pyrimidinyl group, a pyrazinyl group, a pyridazinyl group, a pyrazolyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzimidazolyl group, a benzoxazolyl group and a benzothiazolyl group and the like.

The alkoxy group as a substituent on the hydrocarbon groups may be linear, branched or cyclic, having, for example, 1 to 6 carbon atom(s). Specific examples include a methoxy group, an ethoxy group, an n-propoxy group, an isopropoxy group, an n-butoxy group, a 2-butoxy group, an isobutoxy group, a tert-butoxy group, an n-pentyloxy group, a 2-methyl butoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, a cyclohexyloxy group, a methoxymethoxy group, a 2-ethoxyethoxy group and a 2-methoxy ethoxy methoxy group and the like.

The alkylenedioxy group as a substituent on the hydrocarbon groups includes alkylenedioxy groups having, for example, 1 to 3 carbon atom(s), and specific examples include a methylenedioxy group, an ethylenedioxy group, a trimethylenedioxy group, a propylenedioxy group and an isopropylidenedioxy group and the like.

The aryloxy group as a substituent on the hydrocarbon groups includes aryloxy groups having, for example, 6 to 14 carbon atoms, and specific examples include a phenoxy group, a tolyloxy group, a xylyloxy group, a naphthoxy group and an anthryloxy group and the like.

The aralkyloxy group as a substituent on the hydrocarbon groups includes aralkyloxy groups having, for example, 7 to 12 carbon atoms, and specific examples include a benzyloxy group, a 4-methoxyphenylmethyl group, a 1-phenylethoxy group, a 2-phenylethoxy group, a 1-phenylpropoxy group, a 2-phenylpropoxy group, a 3-phenylpropoxy group, a 1-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, a 3-phenylhexyloxy group, a 4-phenylhexyloxy group, a 5-phenylhexyloxy group and a 6-phenylhexyloxy group and the like.

The heteroaryloxy group as a substituent on the hydrocarbon groups includes, heteroaryloxy groups having, for example, 2 to 14 carbon atoms and containing at least 1, preferably 1 to 3 heteroatoms such as a nitrogen atom, an oxygen atom and a sulfur atom, and specific examples include a 2-pyridyloxy group, a 2-pyrazyloxy group, a 2-pyrimidyloxy group and a 2-quinolyloxy group and the like.

The alkylthio group as a substituent on the hydrocarbon groups includes alkylthio groups which may be linear, branched or cyclic, for example having 1 to 6 carbon atom(s). Specific examples include a methylthio group, an ethylthio group, an n-propylthio group, an isopropylthio group, an n-butylthio group, a 2-butylthio group, an isobutylthio group, a tert-butylthio group, a pentylthio group, a hexylthio group and a cyclohexylthio group and the like.

The arylthio group as a substituent on the hydrocarbon groups includes arylthio groups having, for example, 6 to 14 carbon atoms, and specific examples include a phenylthio group, a tolylthio group, a xylylthio group and a naphthylthio group and the like.

The aralkylthio group as a substituent on the hydrocarbon groups includes, aralkylthio groups having for example 7 to 12 carbon atoms, and specific examples include a benzylthio group and a 2-phenethylthio group and the like.

The heteroarylthio group as a substituent on the hydrocarbon groups includes heteroarylthio groups having, for example, 2 to 14 carbon atoms and containing at least 1, preferably 1 to 3 heteroatoms such as a nitrogen atom, an oxygen atom and a sulfur atom. Specific examples include a 4-pyridylthio group, a 2-benzimidazolylthio group, a 2-benzoxazolylthio group and a 2-benzthiazolylthio group and the like.

The substituted amino group as a substituent on the hydrocarbon groups includes an amino group in which one or two hydrogen atom(s) is substituted with substituent(s) such as an alkyl group, an aryl group and an aralkyl group.

Specific examples of the amino group substituted with an alkyl group(s) as a substituent on the hydrocarbon groups, that is, the alkyl-substituted amino group, include mono- or di-alkylamino groups such as an N-methylamino group, an N,N-dimethylamino group, an N,N-diethylamino group, an N,N-diisopropylamino group and an N-cyclohexylamino group and the like.

Specific examples of the amino group substituted with an aryl group(s) as a substituent on the hydrocarbon groups, that is, the aryl-substituted amino group, include mono- or di-arylamino groups such as an N-phenylamino group, an N,N-diphenylamino group, an N,N-ditolylamino group, an N-naphthylamino group and an N-naphthyl-N-phenylamino group and the like.

Specific examples of the amino group substituted with an aralkyl group(s) as a substituent on the hydrocarbon groups, that is, the aralkyl-substituted amino group, include mono- or di-aralkylamino groups such as an N-benzylamino group and an N,N-dibenzylamino group and the like.

The tri-substituted silyloxy group as a substituent on the hydrocarbon groups includes a trimethylsilyloxy group, a triethylsilyloxy group, a triisopropylsilyloxy group, a tert-butyldimethylsilyloxy group, a tert-butyldiphenylsilyloxy group and a triphenylsilyloxy group and the like.

The halogen atom as a substituent on the hydrocarbon groups includes a fluorine atom, a chlorine atom, a bromine atom and an iodine atom. The halogen-substituted alkyl group includes a monofluoromethyl group, a difluoromethyl group, a trifluoromethyl group and a pentafluoroethyl group and the like.

Preferable substituents which may be substituted on the alkyl group represented by the hydrocarbon group include the above-mentioned alkyl group, alkenyl group, alkynyl group, aryl group, aralkyl group, heterocyclic group, alkoxy group, alkylenedioxy group, aryloxy group, aralkyloxy group, heteroaryloxy group, alkylthio group, arylthio group, aralkylthio group, heteroarylthio group, amino group, substituted amino group, hydroxyl group, nitro group, mercapto group, tri-substituted silyloxy group and halogen atom. Preferable substituents which may be substituted on the alkenyl group represented by the hydrocarbon group include the above-mentioned alkyl group, halogen atom, aryl group and heterocyclic group. Preferable substituents which may be substituted on the alkynyl group represented by the hydrocarbon group include the above-mentioned alkyl group, aryl group and heterocyclic group. Preferable substituents which may be substituted on the aryl group represented by the hydrocarbon group include the above-mentioned alkyl group, aryl group, heterocyclic group and halogen atom.

The heterocyclic group represented by $R^1$, $R^3$, $R^4$, $R^5$, $R^6$, $R^{3'}$, $R^{4'}$, $R^{5'}$, $R^{6'}$, $R^9$, $R^{10}$, $R^{11}$ or $R^{12}$ includes aliphatic or aromatic heterocyclic groups, and specific examples include the heterocyclic groups mentioned as substituents on the hydrocarbon groups. Substituents which may be substituted on these heterocyclic groups include an alkyl group, an aryl group and a heterocyclic group, and specific examples of the respective substituents include the above-mentioned substituents on the hydrocarbon groups described above.

The alkoxy group represented by $R^1$, $R^3$, $R^4$, $R^5$, $R^6$, $R^{3'}$, $R^{4'}$, $R^{5'}$, $R^{6'}$, $R^9$, $R^{10}$, $R^{11}$ or $R^{12}$ includes alkoxy groups which may be linear, branched or cyclic, having for example, 1 to 20 carbon atom(s), preferably 1 to 10 carbon atom(s). Specific examples include a methoxy group, an ethoxy group, an n-propoxy group, an isopropoxy group, an n-butoxy group, a 2-butoxy group, an isobutoxy group, a tert-butoxy group, an n-pentyloxy group, a 2-methylbutoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, a heptyloxy group, an octyloxy group, a nonyloxy group, a decyloxy group, a cyclohexyloxy group, a methoxymethoxy group and a benzyloxy group and the like. Substituents which may be substituted on the alkoxy group include an alkyl group, an aryl group, a halogen atom, a heterocyclic group and an alkoxy group. Specific examples of the respective substituents include above-mentioned substituents on the hydrocarbon groups described above.

The alkoxycarbonyl group represented by $R^1$, $R^3$, $R^4$, $R^5$, $R^6$, $R^{3'}$, $R^{4'}$, $R^{5'}$, $R^{6'}$, $R^9$, $R^{10}$, $R^{11}$ or $R^{12}$ is preferably an alkoxycarbonyl group whose alkoxy moiety may be linear, branched or cyclic, and examples include, but not limited to, an alkoxycarbonyl group having 2 to 20 carbon atoms. Specific examples include a methoxycarbonyl group, an ethoxycarbonyl group, an n-propoxycarbonyl group, an isopropoxycarbonyl group, an n-butoxycarbonyl group, a tert-butoxycarbonyl group, a pentyloxycarbonyl group, a hexyloxycarbonyl group, a 2-ethylhexyloxycarbonyl group, a lauryloxycarbonyl group, a stearyloxycarbonyl group and a cyclohexyloxycarbonyl group and the like. Substituents which may be substituted on the alkoxycarbonyl group include an alkyl group, an aryl group, a halogen atom, a heterocyclic group and an alkoxy group. Specific examples of the respective substituents include the above-mentioned substituents on the hydrocarbon groups described above.

The substituted amino group represented by $R^1$, $R^3$, $R^4$, $R^5$, $R^6$, $R^{3'}$, $R^{4'}$, $R^{5'}$, $R^{6'}$, $R^9$, $R^{10}$, $R^{11}$ or $R^{12}$ includes an amino group in which one or two hydrogen atom(s) is substituted with substituent(s). Specific examples of the substituents on the substituted amino include a hydrocarbon group (for example, an alkyl group or the like), an aryl group, an aralkyl group, an acyl group, an alkoxycarbonyl group, an aryloxycarbonyl group and an aralkyloxycarbonyl group and the like.

Specific examples of the amino group substituted with an alkyl group(s), that is, the alkyl-substituted amino group, include mono- or di-alkylamino groups such as an N-methylamino group, an N,N-dimethylamino group, an N,N-diethylamino group, an N,N-diisopropylamino group, an N-methyl-N-isopropylamino group and an N-cyclohexylamino group and the like.

Specific examples of the amino group substituted with an aryl group(s), that is, the aryl-substituted amino group, include mono- or di-arylamino groups such as an N-phenylamino group, an N,N-diphenylamino group, an N-naphthylamino group, an N-methyl-N-phenylamino group and an N-naphthyl-N-phenylamino group and the like.

Specific examples of the amino group substituted with an aralkyl group(s), that is, the aralkyl-substituted amino group, include mono- or di-aralkylamino groups such as an N-benzylamino group and N,N-dibenzylamino group, and other examples include di-substituted amino groups such as an N-benzyl-N-methylamino group and the like.

Specific examples of the amino group substituted with an acyl group(s), that is, the acylamino group, include a formylamino group, an acetylamino group, a propionylamino group, a pivaloylamino group, a pentanoylamino group, a hexanoylamino group and a benzoylamino group and the like.

Specific examples of the amino group substituted with an alkoxycarbonyl group (s), that is, the alkoxycarbonylamino group, include a methoxycarbonylamino group, an ethoxycarbonylamino group, an n-propoxycarbonylamino group, an n-butoxycarbonylamino group, a tert-butoxycarbonylamino group, a pentyloxycarbonylamino group and a hexyloxycarbonylamino group and the like.

Specific examples of the amino group substituted with an aryloxycarbonyl group(s), that is, the aryloxycarbonylamino group, include an amino group in which one hydrogen in the amino group is substituted with the above-mentioned aryloxycarbonyl group, and specific examples include a phenoxycarbonylamino group and a naphthyloxycarbonylamino group and the like.

Specific examples of the amino group substituted with an aralkyloxycarbonyl group, that is, the aralkyloxycarbonylamino group, include, for example, a benzyloxycarbonylamino group.

The ring formed by arbitrary two groups selected from $R^3$, $R^4$, $R^5$ and $R^6$ or from $R^{3'}$, $R^{4'}$, $R^{5'}$ and $R^{6'}$ in the compounds of the general formulae (1) to (11) includes a ring formed by a combination of $R^3$ and $R^4$, $R^3$ and $R^5$, $R^3$ and $R^6$, $R^4$ and $R^5$, $R^4$ and $R^6$, or $R^5$ and $R^6$, or by a combination of $R^{3'}$ and $R^{4'}$, $R^{3'}$ and $R^{5'}$, $R^{3'}$ and $R^{6'}$, $R^{4'}$ and $R^{5'}$, $R^{4'}$ and $R^{6'}$, or $R^{5'}$ and $R^{6'}$. The formed ring includes a 5- to 20-membered ring which may contain one or two heteroatom(s) such as an oxygen atom and a nitrogen atom as constituent atoms of the ring. Preferable examples of the formed ring include, for example, monocycles such as a cyclopentane ring, a cyclohexane ring, a cycloheptane ring, a cyclooctane ring, a cyclodecane ring, a cyclododecane ring, a cyclotetradecane ring, a cyclopentadecane ring, a cyclohexadecane ring and a cycloheptadecane ring; and condensed rings such as a dihydronaphthalene ring, an indene ring, an indane ring, a dihydroquinoline ring and a dihydroisoquinoline ring. These rings may be substituted with a hydrocarbon group, a heterocyclic group, an alkoxy group, a substituted amino group, and the like. Specific examples of the respective substituents include the above-mentioned hydrocarbon group, heterocyclic group, substituted amino group, and the like.

Examples of the substituted carbamoyl group represented by $R^1$, $R^3$, $R^4$, $R^5$, $R^6$, $R^{3'}$, $R^{4'}$, $R^{5'}$, $R^{6'}$, $R^9$, $R^{10}$, $R^{11}$ or $R^{12}$ include, but not limited to, a methylcarbamoyl group, an isopropylcarbamoyl group, a butylcarbamoyl group and a heptylcarbamoyl group and the like.

The alkyl group represented by $R^2$, $R^7$ or $R^{13}$ is an alkyl group which may be linear, branched or cyclic alkyl group, preferably having for example 1 to 20 carbon atom(s). Specific examples include, but not limited to, linear or branched alkyl groups such as a methyl group, an ethyl group, an n-propyl group, an isopropyl group, an n-butyl group, a sec-butyl group, an isobutyl group, a tert-butyl group, an n-pentyl group, a neopentyl group, a tert-pentyl group, a hexyl group, a heptyl group, an octyl group, a nonyl group, a decyl group, a cetyl group and a stearyl group; and cycloalkyl groups such as a cyclopentyl group, a cyclohexyl group and a cyclooctyl group or the like.

The aryl group represented by $R^2$, $R^7$ or $R^{13}$ includes an aryl group having, for example, 6 to 20 carbon atoms, and specific examples include a phenyl group, a naphthyl group, an anthryl group, a phenanthryl group, a biphenyl group and a terphenyl group and the like.

Examples of the halogen atom represented by $R^1$, $R^3$, $R^4$, $R^5$, $R^6$, $R^{3'}$, $R^{4'}$, $R^{5'}$, $R^{6'}$, $R^9$, $R^{10}$, $R^{11}$ or $R^{12}$ include, but not limited to, a fluorine atom, a chlorine atom, a bromine atom and an iodine atom.

The divalent hydrocarbon group represented by $A^1$, $A^2$ or $A^3$ includes, for example, an alkylene group, an alkenylene group, an alkynylene group and an arylene group. The alkylene group includes, for example, a methylene group, an ethylene group, an isopropylidene group, a trimethylene group, a tetramethylene group, a propylene group, a 1,2-butanediyl group, a pentamethylene group, a hexamethylene group, a 2-ethyl-1,4-butanediyl group, a 2-ethyl-1,6-hexanediyl group, a 1,1,3,3-tetramethyl-1,4-butanediyl group and a methoxyethylene group and the like. The alkenylene group includes, for example, a vinylene group, a propenylene group, a butenylene group and an ethoxyvinylene group and the like. The alkynylene group includes, for example, an ethynylene group, a 3-pentynylene group and a propynylene group and the like. The arylene group includes, for example, a phenylene group, a methylphenylene group, an ethylphenylene group, a propylphenylene group, a butylphenylene group, a methoxyphenylene group, a naphthalenediyl group, a biphenyldiyl group and a binaphthalenediyl group and the like.

The divalent heterocyclic group represented by $A^1$, $A^2$ or $A^3$ is a divalent heterocyclic group (which may be an aliphatic heterocycle, an aromatic heterocycle, a monocycle or a condensed ring) containing at least one heteroatom such as a nitrogen atom, an oxygen atom or a sulfur atom. Preferable examples of the divalent heterocyclic group include a pyridinediyl group, a dibenzothiophenediyl group, a furandiyl group, a thiophenediyl group, an imidazolediyl group, a benzoquinolinediyl group and a benzothiazolediyl group and the like.

The metal element of the metal compound used in the production method of the present invention is a metal element belonging to the group 12 in the periodic table. The metal element is preferably zinc or cadmium, more preferably zinc. Specific metal compounds containing the metal element include, but not limited to, organic acid zinc salts such as zinc acetate, zinc trifluoroacetate, zinc acetoacetate and zinc acetylacetonate; zinc sulfonates such as zinc trifluoromethanesulfonate and zinc p-toluenesulfonate; inorganic zinc substances such as zinc chloride, zinc bromide, zinc nitrate and zinc oxide; organic acid cadmium salts such as cadmium acetate, cadmium stearate, cadmium acetoacetate and cadmium acetylacetonate; inorganic cadmium salts such as cadmium chloride, cadmium bromide, cadmium iodide and cadmium nitrate; organic acid mercury salts such as mercury acetate, mercury benzoate and mercury trifluoroacetate; mercury sulfonates such as mercury trifluoromethanesulfonate; and inorganic mercury salts such as mercury chloride, mercury bromide, mercury iodide and mercury nitrate. When there are hydrates of these metal compounds, the hydrates may also be used in the production method of the present invention.

Multinuclear zinc clusters obtained by heating organic acid zinc salts may also be used in the production method of the present invention.

The multinuclear zinc cluster used in the present invention includes the compounds represented by the general formula (4) wherein a is 4, b is 6, and c or c' is 1. In the compounds represented by the general formula (4), preferable $R^7$ includes, for example, a methyl group, an ethyl group, a trifluoromethyl group and a phenyl group.

Preferable examples of the multinuclear zinc cluster include, but not limited to, $Zn_4(OAc)_6O$, $Zn_4(OCOEt)_6O$, $Zn_4(OPV)_6O$, $Zn_4\{OCO(CH_2)_{16}CH_3\}_6O$, $Zn_4(OCOPh)_6O$ and $Zn_4(OCOCF_3)_6O$, wherein Ac represents an acetyl group, Et represents an ethyl group, Pv represents a pivaloyl group, and Ph represents a phenyl group.

The multinuclear zinc cluster represented by the general formula (4) used in the present invention can be obtained by methods known in the art, for example by a method described on page 986 in "Shin Jikken Kagaku Koza (New Experimental Chemistry Course) 8-II". Specifically, the multinuclear zinc cluster can be obtained by heating a zinc carboxylate such as zinc acetate or zinc trifluoroacetate at about 270° C. or more in vacuum.

The metal compounds including the multinuclear zinc cluster used in the present invention may be used alone or as a mixture of two or more thereof.

The method for producing an azoline compound according to the present invention (for example, a compound represented by the general formula (3) or (5)) can be carried out, for example, by reacting a carboxylic acid or a carboxylic acid derivative represented by the general formula (1) or a nitrile represented by the general formula (8-2) with an aminochalcogenide represented by the general formula (2) in the presence of a compound containing a group 12 metal (preferably zinc) element in the periodic table (hereinafter, the compound containing an group 12 metal element is abbreviated as metal compound; the metal compound is preferably a compound represented by the general formula (4)).

The method for producing a bisazoline compound according to the present invention (for example, a compound represented by the general formula (9) or (9-2)) can be carried out, for example, by reacting a compound represented by the general formula (8) or (8-2) with an aminochalcogenide represented by the general formula (2) or (2-2) in the presence of a metal compound (preferably, a compound represented by the general formula (4)).

The method for producing amides according to the present invention (for example, a compound represented by the general formula (7)) can be carried out, for example, by reacting a carboxylic acid or a carboxylic acid derivative represented by the general formula (1) with amines represented by the general formula (6) in the presence of a metal compound (preferably, a compound represented by the general formula (4)).

The method for producing bisamides according to the present invention (for example, a compound represented by the general formula (7-2)) can be carried out, for example, by reacting dicarboxylic acids represented by the general formula (8-4) with amines represented by the general formula (6) in the presence of a metal compound (preferably, a compound represented by the general formula (4)).

The method for producing cyanoamides according to the present invention (for example, a compound represented by the general formula (7-3)) can be carried out, for example, by reacting cyanocarboxylic acids represented by the general formula (8-2) with amines represented by the general formula (6) in the presence of a metal compound (preferably, a compound represented by the general formula (4)).

In the production method of the present invention, the metal compound can act as a catalyst.

The carboxylic acid or carboxylic acid derivative represented by the general formula (1) includes, but not limited to, carboxylic acids such as acetic acid, propionic acid, butyric acid, isobutyric acid, valeric acid, isovaleric acid, hexanoic acid, cyclopentanecarboxylic acid, cyclohexanecarboxylic acid, benzoic acid, 2-biphenylcarboxylic acid, cinnamic acid, 3-phenylpropionic acid, pyridine-2-carboxylic acid, and 2-(diphenylphosphino)benzoic acid, as well as carboxylates thereof such as methyl esters and ethyl esters. The dicarboxylic acid includes the compounds represented by the general formula (8) or (8-4). Specific examples of the dicarboxylic acid include, but not limited to, dicarboxylic acids such as oxalic acid, malonic acid, succinic acid, glutaric acid, adipic acid, dimethylmalonic acid, 1,1-cyclohexanedicarboxylic acid, phthalic acid, isophthalic acid, terephthalic acid, 2,2'-biphenyldicarboxylic acid, 2,2'-binaphthyldicarboxylic acid, 2,6-pyridinedicarboxylic acid, and 2-hydroxyisophthalic acid, as well as dicarboxylates thereof such as dimethyl esters and diethyl esters. The cyanocarboxylic acids represented by the general formula (8-2) include, but not limited to, cyanoacetic acid, 2-cyano-2-methylpropionic acid, 2-cyanobenzoic acid, 3-cyanobenzoic acid, 4-cyanobenzoic acid, 2-cyanopyridinecarboxylic acid, 3-cyanopyridinecarboxylic acid, and 3-cyano-2-hydroxybenzoic acid, as well as methyl esters or ethyl esters thereof. The carboxylic acid derivative of the general formula (1) wherein $R^1$ and $R^2$ bond to each other to form a ring includes lactones, and examples of such lactones include, but not limited to, γ-butyrolactone, γ-valerolactone, δ-valerolactone, 2-oxetanone, 4-methyl-2-oxetanone, γ-ethyl-γ-butyrolactone, γ-propyl-γ-butyrolactone, δ-methyl-δ-valerolactone, δ-ethyl-δ-valerolactone, and δ-propyl-δ-valerolactone.

Preferable examples of the aminochalcogenide represented by the general formula (2) and the amines represented by the general formula (6) include, but not limited to, 2-aminoethanol, 2-amino-2-phenylethanol, 2-aminopropanol, 2-amino-2-methylpropanol, 2-amino-1,1-dimethylpropanol, 2-amino-3-phenylpropanol, 2-amino-1,1-diphenylpropanol, 2-amino-1,1-di(4-methylphenyl) propanol, 2-amino-1,1-di(4-methoxyphenyl) propanol, 2-amino-1,1-dibenzylpropanol, 1-(1-aminoethyl)cyclohexanol, 2-amino-3-methylbutanol (valinol), 2-amino-3-methyl-1,1-dimethylbutanol, 2-amino-3-methyl-1,1-diphenylbutanol, 2-amino-3-methyl-1,1-di(4-methoxyphenyl) butanol, 1-(1-amino-2-methylpropyl)cyclopentanol, 1-(1-amino-3-methylpropyl)cyclohexanol, 2-amino-3-methylpentanol, 2-amino-4-methylpentanol, 2-amino-4-methyl-1,1-dimethylpentanol, 2-amino-4-methyl-1,1-diphenylpentanol, 2-amino-4-methyl-1,1-di(4-methoxyphenyl) pentanol, 2-amino-4-methyl-1,1-dibenzylpentanol, 1-(1-amino-3-methylbutyl)cyclopentanol, 1-(1-amino-3-methylbutyl)cyclohexanol, 2-amino-3,3-dimethylbutanol, 2-amino-3,3-dimethyl-1,1-dimethylbutanol, 2-amino-3,3-dimethyl-1,1-di(4-methoxyphenyl) butanol, 1-(1-amino-2,2-dimethylpropyl) cyclohexanol, 2-amino-2-phenyl-1,1-dimethylethanol, 2-amino-2-phenyl-1,1-diphenylethanol, 2-amino-2-phenyl-1,1-di(4-methylphenyl)ethanol, 2-amino-2-phenyl-1,1-di(4-methoxyphenyl)ethanol, 2-amino-2-phenyl-1,1-dibenzylethanol, 2-amino-2-(2-naphthyl)ethanol, 2-amino-2-(1-naphthyl)-1,1-diethylethanol, 2-amino-2-(2-naphthyl)-1,1-di-(4-methylphenyl)ethanol, 2-amino-2-(1-naphthyl)-1,1-di-(4-methoxyphenyl)ethanol, 2-amino-2-(2-naphthyl)-1,1-dibenzylethanol, 1-amino-1-(2-naphthyl)methyl) cyclopentanol, 1-amino-1-(1-naphthyl)methyl) cyclohexanol, 2-amino-3-phenyl-1,1-diethylpropanol, 2-amino-3-phenyl-1,1-diphenylpropanol, 2-amino-3-phenyl-1,1-di(4-methylphenyl) propanol, 2-amino-3-phenyl-1,1-di(4-methoxyphenyl) propanol, 1-(1-amino-2-phenylethyl)cyclopentanol, 1-(1-amino-2-phenylethyl) cyclohexanol, 2-amino-3-(3-indolyl) propanol, 2-amino-3-(4-hydroxyphenyl) propanol, 1-amino-2-indanol, methylamine, ethylamine, propylamine, isopropylamine, butylamine, amylamine, aniline, toluidine, benzylamine, 1-phenylethylamine, 1-phenyl-2-naphthylamine, and allylamine. These aminochalcogenides and amines may be racemates or optically active substances thereof.

The amount of the metal compound used in the method for producing the azoline compound, bisazoline compound, amides, bisamides or cyanoamides is not particularly limited, but the metal compound is generally used in such an amount that the metal atom therein is in a molar ratio of preferably about 0.001 to 0.5, more preferably about 0.01 to 0.3, relative to 1 mol of the carboxylic acid or carboxylic acid derivative as the starting material.

The ratio of the carboxylic acid, carboxylic acid derivative, dicarboxylic acid, dicarboxylic acid derivative or nitrites as the starting material to the aminochalcogenide used in the method for producing an azoline compound and a bisazoline compound according to the present invention (hereinafter also referred to collectively as azolines) is not particularly limited, but is generally as follows: when the carboxylic acid, the carboxylic acid derivative and the nitrites as the starting material are a monocarboxylic acid, a monocarboxylic acid derivative and a nitrile respectively, the molar ratio of the monocarboxylic acid, monocarboxylic acid derivative or nitrile to the aminochalcogenide is preferably about 0.5 to 2.0, more preferably 0.7 to 1.5.

When the carboxylic acid, the carboxylic acid derivative and the nitrile as the starting material are a dicarboxylic acid and a dicarboxylic acid derivative, respectively, the amount of the aminochalcogenide used may be naturally made twice as high as the amount of the aminochalcogenide for the monocarboxylic acid or monocarboxylic acid derivative described above.

In the method for producing amides, bisamides or cyanoamides according to the present invention (hereinafter also referred to collectively as amide compound), the ratio of the carboxylic acid and the carboxylic acid derivative, the dicarboxylic acid or the cyanocarboxylic acid to the amines (for example, the compound represented by the general formula (6)) as the starting materials may be established such that when the carboxylic acid and carboxylic acid derivative are a monocarboxylic acid and a monocarboxylic acid derivative respectively, the amount of either the carboxylic acid, carboxylic acid derivative or cyanocarboxylic acids, or amines as the starting material may be the equivalent or larger amount of the others, but it is preferable that the starting material used in a larger amount is one which when remaining in excess in the system, can be easily removed at the time of post-treatment after the reaction. When the carboxylic acid and carboxylic acid derivative are a dicarboxylic acid and a dicarboxylic acid derivative, respectively, the ratio of the amine used may be naturally made twice as high as the ratio of the amines used for the monocarboxylic acid.

The reaction in the method for producing an azoline or an amide compound according to the present invention is carried out usually in a solvent, and specific examples of the solvent include, but not limited to, aromatic solvents such as toluene, xylene and chlorobenzene; aliphatic hydrocarbon solvents such as hexane, heptane and octane; ether solvents such as diethyl ether, diisopropyl ether, tert-butyl methyl ether, tetrahydrofuran and 1,4-dioxane; amide solvents such as dimethylformamide (DMF), dimethylacetamide (DMAc) and N-methylpyrrolidone (NMP); and dimethylsulfoxide (DMSO). Among them, the aromatic solvents are preferable.

The reaction in the method for producing an azoline or an amide compound according to the present invention can be carried out in the air or under an inert gas atmosphere such as a nitrogen gas or an argon gas. The reaction time is not particularly limited, but is generally about 1 to 45 hours, preferably about 6 to 18 hours. The reaction temperature is not particularly limited, but is generally room temperature to about 150° C., preferably 50 to 150° C., more preferably about 80 to 130° C. These conditions may be suitably altered depending on the type and amount of the starting materials used, etc.

After the reaction in the method for producing azolines or an amide compound according to the present invention, a generally used post-treatment (for example, concentration, solvent exchange, chromatography, crystallization or the like) can be carried out to obtain the objective azolines or amide compounds. It goes without saying that when the starting material aminochalcogenide or amines is a racemate or an optically active substance, a racemate or an optically active azolines or amide compound corresponding to the starting material is obtained.

The method for producing a peptide (for example, a compound represented by the general formula (11)) according to the present invention is carried out by subjecting the same or different amino acids represented by the general formula (10) to intermolecular condensation in the presence of a zinc compound (preferably a compound represented by the general formula (4)), preferably in a solvent inert to the reaction.

In the case of the amino acids and peptides represented by the general formulae (10) and (11), respectively, the integer represented by n is preferably 0 to 10, more preferably 1 to 6.

In the case of the peptides represented by the general formula (11), an integer of 1 or more represented by m is preferably 1 to 10.

In the peptides represented by the general formula (11), a plurality of $R^9$s or $R^{10}$s are present when n is 0 to 10, and a plurality of $R^{11}$s or $R^{12}$s are present when n is 1 to 10, the plurality of $R^9$s, $R^{10}$s, $R^{11}$s or $R^{12}$s may be same or different, respectively. For example, when m is 1, there are two $R^9$s for example, and when one of the two $R^9$s is, for example, a hydrogen atom, the other $R^9$ can be a hydrogen atom, a hydrocarbon group, an alkoxy group, an alkoxycarbonyl group, a halogen atom, a substituted amino group, a substituted carbamoyl group or a heterocyclic group. This also applies to $R^{10}$, $R^{11}$ or $R^{12}$, and also applies to the case when m is 2 or more.

As used herein, "subjecting to intermolecular condensation" refers to subjecting to dehydration condensation between a carboxyl group of one amino acid molecule and an amino group of another amino acid molecule to form a peptide bond between the two molecules. More specifically, the intermolecular condensation means that a plurality of the same or different amino acids represented by the general formula (10) are bound to one another via peptide bonds.

The solvent inert to the above reaction includes, for example, aromatic solvents such as toluene, xylene and chlorobenzene; aliphatic hydrocarbon solvents such as hexane, heptane and octane; ether solvents such as diethyl ether, diisopropyl ether, tert-butylmethylether, tetrahydrofuran and 1,4-dioxane; amide solvents such as dimethylformamide (DMF), dimethylacetamide (DMAc) and N-methylpyrrolidone (NMP); and dimethylsulfoxide (DMSO). Among them, the aromatic solvents are preferable. The reaction time is not particularly limited, but is generally about 1 to 45 hours, preferably 6 to 18 hours. The reaction temperature is not particularly limited, but is usually room temperature to about 150° C., preferably 50 to 150° C., more preferably about 80 to 130° C. These conditions can be suitably altered depending on the type and amount of the starting materials used, etc.

As the amino acids used in the method for producing peptides according to the present invention, one or more kinds of amino acids are used. When two or more kinds of amino acids are used, peptides condensed in a regular, random or block form are obtained.

The above-mentioned carboxylic acid, carboxylic acid derivative, biscarboxylic acids, nitrile, aminochalcogenide and amines used as the starting materials in the method of the present invention may be commercially available compounds, or can be produced by methods known in the art.

(II) Compound of the Invention

The oxazoline compound represented by the general formula (13) below is a novel compound not described in any literature.

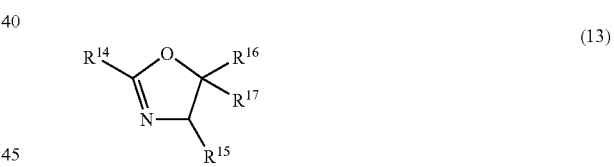

(13)

(wherein $R^{14}$ represents an alkyl group having 4 to 20 carbon atoms, an optionally substituted phenyl group, a hydroxyalkyl group having 2 to 6 carbon atoms, or a phenylalkyl group whose alkyl moiety has 2 to 10 carbon atoms, $R^{15}$ represents an alkyl group having 2 to 6 carbon atoms, an optionally substituted phenyl group, or a phenylalkyl group whose alkyl moiety has 1 to 6 carbon atom(s), $R^{16}$ and $R^{17}$ may be the same or different and each represents a hydrogen atom or an alkyl group having 1 to 6 carbon atom(s), and $R^{15}$, together with $R^{16}$ or $R^{17}$, may form a ring).

As described above, $R^{14}$ may be a linear, branched or cyclic alkyl group having 4 to 20 carbon atoms. Specific examples include linear or branched alkyl groups such as a methyl group, an ethyl group, an n-propyl group, an isopropyl group, an n-butyl group, a sec-butyl group, an isobutyl group, a tert-butyl group, an n-pentyl group, a neopentyl group, a tert-pentyl group, a hexyl group, a heptyl group, an octyl group, a nonyl group, a decyl group, a cetyl group and a stearyl group; and cycloalkyl groups such as a cyclopentyl group, a methylcyclopentyl group, a cyclohexyl group, a methylcyclohexyl group and a cyclooctyl group. $R^{14}$ is particularly preferably an alkyl having 6 to 17 carbon groups.

As described above, $R^{14}$ may be, for example, a phenyl group which may have 1 to 3 substituent(s). The substituents include an alkoxycarbonyl group (a methoxycarbonyl group, an ethoxycarbonyl group or the like), a hydroxyalkyl group (a hydroxymethyl group, a 2-hydroxyethyl group or the like), a hydroxyl group, a cyano group and the like. The hydroxyalkyl group and the hydroxyl group may be protected with protective groups, and the protective groups include a methoxymethyl group, a methoxyethyl group, a trimethylsilyl group, a t-butyldimethylsilyl group, and the like.

As described above, $R^{14}$ may be a linear or branched hydroxyalkyl group having 2 to 6 carbon atoms, preferably 3 to 6 carbon atoms, more preferably 3 to 5 carbon atoms.

As described above, $R^{14}$ may be a phenylalkyl group whose alkyl moiety has 2 to 10 carbon atoms. $R^{14}$ is particularly preferably a benzyl group or a phenethyl group, more preferably a phenethyl group.

As described above, $R^{15}$ may be a linear or branched alkyl group having 2 to 6 carbon atoms. Such alkyl group includes the same alkyl group as described for $R^{14}$. $R^{15}$ is particularly preferably a branched alkyl group, more preferably an isopropyl group, a sec-butyl group or a tert-butyl group, still more preferably a sec-butyl group or a tert-butyl group.

As described above, $R^{15}$ may be, for example, a phenyl group having 1 to 3 substituent(s). The substituents include an alkyl group having 1 to 6 carbon atom(s) and an alkoxy group having 1 to 6 carbon atom(s).

As described above, $R^{15}$ may be a phenylalkyl group whose alkyl moiety has 1 to 6 carbon atom(s). $R^{15}$ is particularly preferably a benzyl group or a phenethyl group, more preferably a benzyl group.

As described above, $R^{16}$ and $R^{17}$ may be same or different and each represents a hydrogen atom or an alkyl group having 1 to 6 carbon atom(s). $R^{16}$ or $R^{17}$ is particularly preferably a hydrogen atom or a methyl group. $R^{15}$, together with $R^{16}$ or $R^{17}$ may form a ring.

Preferable among the compounds described above are those compounds wherein $R^{14}$ is an alkyl group having 4 to 20 carbon atoms, an optionally substituted phenyl group, or a hydroxyalkyl group having 2 to 6 carbon atoms; $R^{15}$ is a linear or branched alkyl group having 2 to 6 carbon atoms; and each of $R^{16}$ and $R^{17}$ is a hydrogen atom.

Also preferable are those compounds wherein $R^{14}$ is a phenylalkyl group whose alkyl moiety has 2 to 10 carbon atoms; $R^{15}$ is either a phenyl group having for example 1 to 3 substituents or a phenylalkyl group whose alkyl moiety has 1 to 6 carbon atom(s); and $R^{16}$ and $R^{17}$ independently represent a hydrogen atom or a methyl group.

The compound of the general formula (13) may be an optically active substance with respect to any one of asymmetric carbon atoms.

EXAMPLES

The present invention will be described in more detail by Examples, but the present invention is not limited thereto.

The instruments used in analysis of compounds in Examples are as follows:
$^1$H NMR (300 MHz), $^{13}$C NMR (75 Hz), $^{19}$F NMR (282 Hz): Varian MERCURY 300
MS (EI), HRMS (EI): JEOL JMS-700.
IR: Jasco FT/IR-230 and Jasco FT/IR-410
Elementary analysis: Perkin-Elmer 2400II.
Melting point (mp): Yanaco micro melting point apparatus.
Optical rotation: Jasco DIP-370 digital polarimeter.

Gas chromatography (GC): Shimadzu Gas Chromatograph GC-14A
Capillary column: DB-5
The yield of each compound was measured by gas chromatography (GC) with n-dodecane or n-nonadecane as an internal standard material.
Compounds not given physical property data were identified by comparison with known physical property data.

Example 1

Production of Oxazolines

Under an argon atmosphere, a mixture of methyl benzoate (1.5 mmol), (L)-valinol (1.8 mmol), $Zn_4(OCOCF_3)_6O$ (0.15 mmol in terms of the number of moles of zinc atom; the number of moles of the zinc compound used in the following Examples is also shown in terms of the number of moles of zinc atom) and chlorobenzene (2.5 mL) was heated under reflux for 12 hours. From the resulting solution, the solvent was removed using an evaporator, and the residues were purified by silica gel column chromatography (hexane/ethyl acetate=10/1 (V/V)) to give (S)-4-isopropyl-2-phenyl-1,3-oxazoline in 83% yield.

The analysis data of the resulting compound and the structural formula of the compound identified thereby are as follows:

State: colorless oil
IR (neat NaCl, v/cm$^{-1}$) 1652, 1450, 1354, 1081, 1065, 1026, 968, 694;
$^1$H NMR (300 MHz, CDCl$_3$, 35° C.) δ 0.91 (d, J=6.9 Hz, 3H, CH(CH$_3$)$_2$), 1.01 (d, J=6.9 Hz, 3H, CH(CH$_3$)$_2$), 1.8-1.9 (m, 1H, CH(CH$_3$)$_2$), 4.08 (m, 2H, CH$_2$O), 4.35 (m, 1H, CHCH$_2$), 7.39 (m, 3H, Ar), 7.73 (dd, J=8.4, 1.8 Hz, 2H, Ar);
$^{13}$C NMR (75 MHz, CDCl$_3$, 35° C.) δ 18.06, 18.83, 32.77, 69.93, 72.52, 127.97, 127.98, 130.80, 162.94;
MS (EI) m/z (relative intensity) 190 ([M$^+$+H], 17), 189 (100), 174 (12), 162 (28);
HRMS (EI) m/z calcd. for C$_{12}$H$_{15}$NO, 189.1154; found 189.1147;
$[α]^{25}_{589}$-61.1 (c 0.39, CH$_2$Cl$_2$).

Examples 2 to 32

Production of Oxazolines

According to the following scheme:

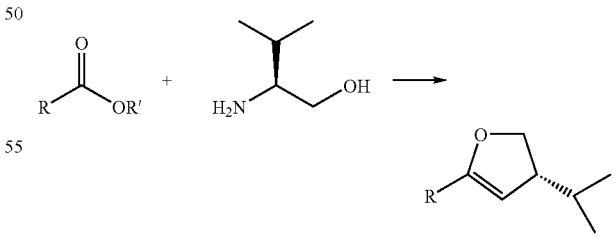

(wherein R and R' represent a functional group shown in Table 1 below), the reaction was carried out in the same manner as in Example 1 except that esters and carboxylic acids shown in Table 1 were used in place of methyl benzoate in Example 1, and metal compounds shown in Table 1 were used in place of $Zn_4(OCOCF_3)_6O$. The yields of the resulting oxazolines are shown in Table 1.

The number of moles of each of the substrates (esters and carboxylic acids) used in Examples 16 to 32 is 3 mmol.

In Table, symbol Ph represents a phenyl group, symbol Cy represents a cyclohexyl group, symbol Bu represents a butyl group, symbol Me represents a methyl group, symbol Et represents an ethyl group, symbol Boc represents a t-butoxycarbonyl group, symbol Bn represents a benzyl group, symbol Ac represents an acetyl group, symbol MEM represents methoxyethoxymethyl, and symbol TBDMS represents a t-butyldimethylsilyl group (these definitions hereinafter apply).

TABLE 1

| Example | R | R' | Catalysts | Yield (%) |
|---|---|---|---|---|
| 2 | Ph | H | $Zn_4(OAc)_6O$ | 28 |
| 3 | Ph | H | $Zn_4(OCOCF_3)_6O$ | 29 |
| 4 | Ph | Me | $Zn_4(OAc)_6O$ | 33 |
| 5 | Ph | Me | $Zn_4(OCOCF_3)_6O$ | 83 |
| 6 | Ph | Et | $Zn_4(OAc)_6O$ | 35 |
| 7 | Ph | Et | $Zn_4(OCOCF_3)_6O$ | 55 |
| 8 | Ph | Me | $ZnCl_2$ | 46 |
| 9 | Ph | Me | ZnO | 19 |
| 10 | Ph | Me | $Zn(OAc)_2$ | 40 |
| 11 | Ph | Me | $Cd(OAc)_2 \cdot 2H_2O$ | 43 |
| 12 | Cy | H | $Zn_4(OAc)_6O$ | 67 |
| 13 | Cy | H | $Zn_4(OCOCF_3)_6O$ | 62 |
| 14 | Cy | Me | $Zn_4(OAc)_6O$ | 60 |
| 15 | Cy | Me | $Zn_4(OCOCF_3)_6O$ | 51 |
| 16 | n-Bu | H | $Zn_4(OAc)_6O$ | Quantitative |
| 17 | n-Bu | H | $Zn_4(OCOCF_3)_6O$ | Quantitative |
| 18 | n-Bu | Me | $Zn_4(OAc)_6O$ | 84 |
| 19 | n-Bu | Me | $Zn_4(OCOCF_3)_6O$ | Quantitative |
| 20 | $C_{17}H_{35}$ | Me | $Zn_4(OCOCF_3)_6O$ | 80 |
| 21 | Ph-CH=CH— | Me | $Zn_4(OCOCF_3)_6O$ | 34 |
| 22 | 3-Cyanophenyl | H | $Zn_4(OCOCF_3)_6O$ | 57 |
| 23 | 4-Cyanophenyl | H | $Zn_4(OCOCF_3)_6O$ | 50 |
| 24 | 3-Bromophenyl | H | $Zn_4(OCOCF_3)_6O$ | 64 |
| 25 | 3-Bromophenyl | Me | $Zn_4(OCOCF_3)_6O$ | 73 |
| 26 | 4-Nitrophenyl | H | $Zn_4(OCOCF_3)_6O$ | 86 |
| 27 | 4-Nitrophenyl | Me | $Zn_4(OCOCF_3)_6O$ | 71 |
| 28 | 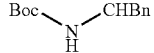 | Me | $Zn_4(OCOCF_3)_6O$ | 23 |
| 29 | 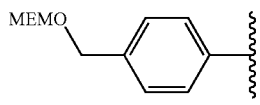 | Me | $Zn_4(OCOCF_3)_6O$ | 75 |
| 30 | 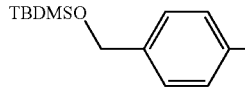 | Me | $Zn_4(OCOCF_3)_6O$ | 87 |
| 31 | 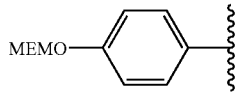 | Me | $Zn_4(OCOCF_3)_6O$ | 74 |
| 32 | 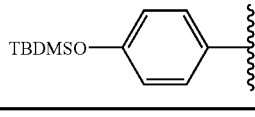 | Me | $Zn_4(OCOCF_3)_6O$ | 70 |

Examples 1 to 11

(S)-4-Isopropyl-2-phenyloxazoline

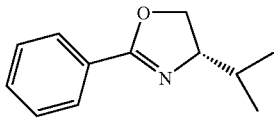

State: colorless oil

IR (neat NaCl, v/cm$^{-1}$) 1652, 1450, 1354, 1081, 1065, 1026, 968, 694;

$^1$H NMR (300 MHz, CDCl$_3$, 35° C.) δ 0.91 (d, J=6.9 Hz, 3H, CH(CH$_3$)$_2$), 1.01 (d, J=6.9 Hz, 3H, CH(CH$_3$)$_2$), 1.8-1.9 (m, 1H, CH(CH$_3$)$_2$), 4.08 (m, 2H, CH$_2$O), 4.35 (m, 1H, CHCH$_2$), 7.39 (m, 3H, Ar), 7.73 (dd, J=8.4, 1.8 Hz, 2H, Ar);

$^{13}$C NMR (75 MHz, CDCl$_3$, 35° C.) δ 18.06, 18.83, 32.77, 69.93, 72.52, 127.97, 127.98, 130.80, 162.94;

MS (EI) m/z (relative intensity) 190 ([M$^+$+H], 17), 189 (100), 174 (12), 162 (28);

HRMS (EI) m/z calcd. for C$_{12}$H$_{15}$NO, 189.1154; found 189.1147;

[α]$^{25}_{589}$-61.1 (c 0.39, CH$_2$Cl$_2$).

Examples 16 to 19

(S)-2-Butyl-4-isopropyloxazoline

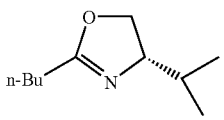

State: colorless oil

IR (neat NaCl, v/cm$^{-1}$) 2959, 1672, 1468, 1384, 1365, 1236, 1173, 984;

$^1$H NMR (300 MHz, CDCl$_3$, 35° C.) δ 0.87 (d, J=6.9 Hz, 3H, CH(CH$_3$)$_2$), 0.92 (t, J=7.2 Hz, 3H, CH$_3$CH$_2$), 0.95 (d, J=6.9 Hz, 3H, CH(CH$_3$)$_2$), 1.37 (m, 2H, CH$_3$CH$_2$CH$_2$), 1.59 (m, 2H, CH$_3$CH$_2$), 1.64 (sept like, 1H, CH(CH$_3$)$_2$), 2.27 (t, J=7.2, 2H, CH$_2$C), 3.91 (m, 2H, CH$_2$O), 4.18 (m, 1H, CHCH$_2$);

$^{13}$C NMR (75 MHz, CDCl$_3$, 35° C.) δ 13.62, 17.95, 18.64, 22.29, 28.26, 32.48, 69.54, 71.93, 167.14;

MS (EI) m/z 169 ([M]$^+$, 13), 168 (66), 126 (100);

HRMS (EI) m/z calcd. for C$_{10}$H$_{19}$NO, 169.1467; found 169.1440;

[α]$^{25}_{589}$-64.9 (c 1.0, CH$_2$Cl$_2$).

Example 20

(S)-2-Heptadecyl-4-isopropyloxazoline

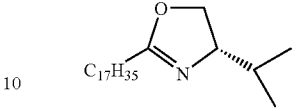

State: white solid

Melting point: 33 to 34° C.;

IR (neat NaCl, v/cm$^{-1}$) 2919, 2848, 1672, 1469, 1378, 1216, 978, 923, 903, 719;

$^1$H NMR (300 MHz, CDCl$_3$, 35° C.) δ 0.8-0.9 (m, 2H, CH$_2$), 0.87 (d, J=6.6 Hz, 3H, CH(CH$_3$)$_2$), 0.95 (d, J=6.6 Hz, 3H, CH(CH$_3$)$_2$), 1.26 (br, 29H, CH$_3$, CH$_2$), 1.5-1.7 (m, 2H, CH$_2$), 1.7-1.8 (m, 1H, CH(CH$_3$2), 2.26 (t, J=7.8 Hz, 2H, CH$_2$-oxazoline), 3.8-4.0 (m, 2H, NCHCH$_2$), 4.1-4.2 (m, 1H, NCHCH$_2$);

$^{13}$C NMR (75 MHz, CDCl$_3$, 35° C.) δ 14.15, 18.10, 18.81, 22.75, 26.31, 28.20, 29.31, 29.41, 29.54, 29.65, 29.71, 29.75, 31.98, 32.62, 69.69, 72.58, 167.32;

MS (EI) m/z 351 ([M]$^+$, 16), 322 (11), 309 (61), 308 (100), 293 (11), 280 (14), 167 (11); HRMS (EI) m/z calcd. for C$_{23}$H$_{45}$NO, 351.3518; found 351.3501;

[α]$^{25}_{589}$-33.3 (c 1.0, CH$_2$Cl$_2$).

Example 22

(S)-2-(3-Cyanophenyl)-4-isopropyloxazoline

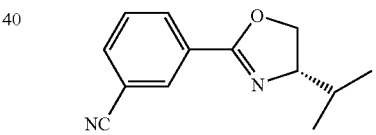

State: white solid

IR (film NaCl, v/cm$^{-1}$) 2958, 2229, 1655, 1483, 1356, 1267, 1177, 1074, 971, 817, 721;

$^1$H NMR (300 MHz, CDCl$_3$, 35° C.) δ 0.94 (d, J=6.9 Hz, 3H, CH(CH$_3$)$_2$), 1.03 (d, J=6.9 Hz, 3H, CH(CH$_3$)$_2$), 1.8-1.9 (m, 1H, CH(CH$_3$)$_2$), 4.1-4.2 (m, 2H, 5-$^{iPr}$oxazoline), 4.4-4.5 (m, 1H, 4-$^{iPr}$oxazoline), 7.52 (dd, J=7.8, 7.8 Hz, 1H, 5-Ar), 7.73 (ddd, J=7.8, 1.8, 1.5 Hz, 1H, 4-Ar), 8.18 (ddd, J=7.8, 1.8, 1.5 Hz, 1H, 6-Ar), 8.25 (dd, J=1.5, 1.5 Hz, 1H, 2-Ar);

$^{13}$CNMR (75 MHz, CDCl$_3$, 35° C.) δ 18.27, 18.89, 32.88, 70.66, 72.86, 112.69, 117.96, 129.05, 129.29, 131.76, 132.14, 134.08, 161.22;

MS (EI) m/z (relative intensity) 214 ([M]$^+$, 5), 171 (100), 143 (32);

HRMS (EI) m/z calcd. for C$_{13}$H$_{14}$N$_2$O, 214.1106; found 214.1084;

[α]$^{25}_{589}$-71.9 (c 1.0, CHCl$_3$).

Example 23

(S)-2-(4-Cyanophenyl)-4-isopropyloxazoline

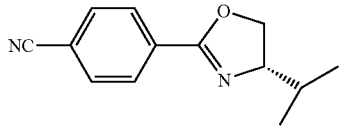

State: white solid
IR (KBr, v/cm$^{-1}$): 2233 (CN), 1643 (C=N);
$^1$H NMR (300 MHz, CDCl$_3$, 35° C.) δ 0.94 (d, J=6.9 Hz, 3H, CH(CH$_3$)$_2$), 1.03 (d, J=6.9 Hz, 3H, CH(CH$_3$)$_2$), 1.85 (sept like, 1H, CH(CH$_3$)$_2$), 4.15 (m, 2H, CH$_2$O), 4.45 (m, 1H, CHCH$_2$), 7.68 (d, J=6.6 Hz, 2H, Ar), 8.05 (d, J=8.4 2H, Ar);
$^{13}$C NMR (75 MHz, CDCl$_3$, 35° C.) δ 18.29, 18.93, 32.92, 70.67, 72.97, 114.60, 118.19, 128.70, 131.93, 132.04.

Examples 24 to 25

(S)-2-(4-Bromophenyl)-4-isopropyloxazoline

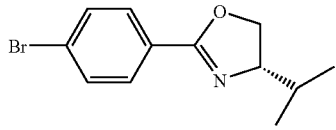

State: white solid
Melting point: 69 to 70° C.;
IR (film NaCl, v/cm$^{-1}$) 2956, 1649, 1396, 1351, 1076, 1008, 964, 831, 665;
$^1$H NMR (300 MHz, CDCl$_3$, 35° C.) δ 0.92 (d, J=6.6 Hz, 3H, CH(CH$_3$)$_2$), 1.02 (d, J=6.6 Hz, 3H, CH(CH$_3$)$_2$), 1.8-1.9 (m, 1H, CH(CH$_3$)$_2$), 4.1-4.2 (m, 2H, NCHCH$_2$), 4.3-4.4 (m, 1H, NCHCH$_2$), 7.52 (d, J=8.4 Hz, 2H, Ar), 7.81 (d, J=8.4 Hz, 2H, Ar),
$^{13}$C NMR (75 MHz, CDCl$_3$, 35° C.) δ 18.23, 18.98, 32.91, 70.33, 72.80, 125.67, 126.89, 129.69, 131.40, 162.36;
MS (EI) m/z (relative intensity) 269 ([M($^{81}$Br)$^+$], 5), 226 (78), 224 (79);
HRMS (EI) m/z calcd. for C$_{12}$H$_{14}$$^{79}$BrNO, 267.0259; found 267.0234; calcd. for C$_{12}$H$_{14}$$^{81}$BrNO, 269.0239; found 269.0236;
[α]$^{25}$$_{589}$-50.6 (c 1.0, CHCl$_3$).

Examples 26 to 27

(S)-4-Isopropyl-2-(4-nitrophenyl) oxazoline

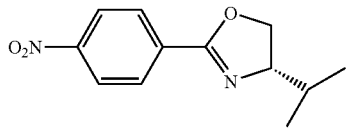

State: whitish yellow solid
Melting point: 54 to 55° C.;
IR (film NaCl, v/cm$^{-1}$) 2968, 1647, 1597, 1523, 1346, 1079, 966, 865, 850, 699;
$^1$H NMR (300 MHz, CDCl$_3$, 35° C.) δ 0.95 (d, J=6.9 Hz, 3H, CH(CH$_3$)$_2$), 1.05 (d, J=6.9 Hz, 3H, CH(CH$_3$)$_2$), 1.8-1.9 (m, 1H, CH(CH$_3$)$_2$), 4.1-4.2 (m, 2H, NCHCH$_2$), 4.4-4.5 (m, 1H, NCHCH$_2$), 8.11 (d, J=8.7 Hz, 2H, Ar), 8.20 (d, J=8.7 Hz, 2H, Ar),
$^{13}$C NMR (75 MHz, CDCl$_3$, 35° C.) δ 18.27, 18.86, 32.88, 70.73, 73.03, 123.25, 129.06, 133.65, 149.26, 161.29;
MS (EI) m/z (relative intensity) 234 ([M$^+$], 5), 191 (100), 163 (19), 117 (18);
HRMS (EI) m/z calcd. for C$_{12}$H$_{14}$N$_2$O$_3$, 234.1004; found 234.1032;
[α]$^{25}$$_{589}$-60.5 (c 1.0, CHCl$_3$).

Example 28

(4S)-2-(1-N-Boc-amino-2-phenylethyl)-4-isopropyloxazoline

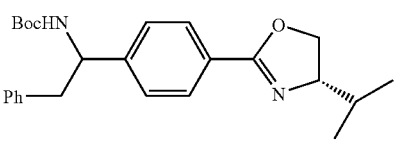

State: white solid
$^1$H NMR (300 MHz, CDCl$_3$, 35° C.) δ 0.78 (d, J=6.6 Hz, 3H, CH(CH$_3$)$_2$), 0.83 (d, J=6.6 Hz, 3H, CH(CH$_3$)$_2$), 0.84 (d, J=6.6 Hz, 3H, CH(CH$_3$)$_2$), 0.85 (d, J=6.6 Hz, 3H, CH(CH$_3$)$_2$), 1.41 (s, 18H, C(CH$_3$)$_3$), 1.66 (2 septetlike peaks, 2H, CH(CH$_3$)$_2$), 2.98, 3.02 (m, 4H, benzyl), 3.7-3.9 (m, 2H, CH$_2$), 3.9-4.0 (m, 2H, CH$_2$), 4.23 (m, 2H, CH), 4.61 (br, 2H, OH), 5.1-5.2 (br 2 peaks, 2H, NHBoc), 7.1-7.3 (m, 10H, Ph);
$^{13}$C NMR (75 MHz, CDCl$_3$, 35° C.) δ 18.18, 18.25, 18.71, 18.88, 28.37, 32.51, 32.60, 49.91, 70.68, 70.74, 71.90, 71.96, 79.53, 126.53, 126.61, 128.06, 128.16, 129.38, 129.56, 136.27, 136.32, 165.62;
MS (EI) m/z 242 ([M]$^+$, 100), 200 (10), 199 (39);
HRMS (EI) m/z calcd. for C$_{12}$H$_{15}$NO, 242.1630; found 242.1601.

Example 29

(S)-4-Isopropyl-2-[p-(methoxyethoxymethoxymethyl)phenyl]oxazoline

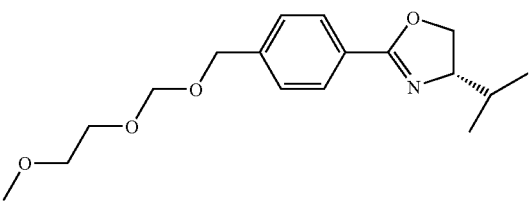

State: colorless oil
IR (KBr disk, v/cm$^{-1}$) 2963, 2890, 1721, 1668, 1651, 1456, 1363, 1049;
$^1$H NMR (300 MHz, CDCl$_3$, 35° C.) δ 0.91 (d, J=6.9 Hz, 3H, CH(CH$_3$)$_2$), 1.02 (d, J=7.2 Hz, 3H, CH(CH$_3$)$_2$), 1.8-1.9

(m, 1H, CH(CH$_3$)$_2$), 3.36 (s, 3H, CH$_3$O(CH$_2$)$_2$OCH$_2$O), 3.5-3.7 (m, 4H, CH$_3$O(CH$_2$)$_2$OCH$_2$O), 4.0-4.1 (m, 2H, NCHCH$_2$O), 4.3-4.4 (m, 1H, NCHCH$_2$O), 4.63 (s, 2H, CH$_3$O(CH$_2$)$_2$OCH$_2$O), 4.78, (s, 2H, MEMOCH$_2$Ar), 7.37 (d, J=8.1 Hz, 2H, Ar), 7.93 (d, J=8.1 Hz, 2H, Ar);

$^{13}$C NMR (75 MHz, CDCl$_3$, 35° C.) δ 17.93, 18.70, 32.65, 58.65, 66.77, 68.59, 69.80, 71.53, 72.37, 94.65, 126.92, 127.02, 127.96, 140.95, 162.69;

MS (FAB) m/z 309 ([M+H]$^+$, 28), 308 (100), 225 (15), 210 (15);

HRMS (FAB) m/z calcd. for C$_{17}$H$_{27}$NO$_4$, 309.1940; found 309.1862;

$[\alpha]^{25}_{589}$-23.4 (c 1.1, CH$_2$Cl$_2$).

Example 30

(S)-4-Isopropyl-2-[p-(tert-butyldimethylsilyloxymethyl) phenyl]oxazoline

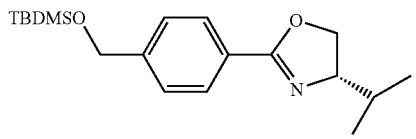

State: colorless oil

IR (neat NaCl, v/cm$^{-1}$) 2956, 2857, 1651, 1470, 1360, 1256, 1116, 1074, 838, 777, 726, 671;

$^1$H NMR (300 MHz, CDCl$_3$, 35° C.) δ 0.20 (s, 6H, $^t$BuMe$_2$Si), 1.03 (d, J=6.6 Hz, 3H, CH(CH$_3$)$_2$), 1.05 (s, 9H, $^t$BuMe$_2$Si), 1.30 (d, J=6.6 Hz, 3H, CH(CH$_3$)$_2$), 1.9-2.0 (m, 1H, CH(CH$_3$)$_2$), 4.1-4.2 (m, 2H, NCHCH$_2$), 4.4-4.5 (m, 1H, NCHCH$_2$), 4.87 (s, TBDMSCH$_2$), 7.45 (d, J=8.1 Hz, 2H, Ar), 8.02 (d, J=8.1 Hz, 2H, Ar);

$^{13}$C NMR (75 MHz, CDCl$_3$, 35° C.) δ −5.14, 18.17, 18.47, 19.01, 25.99, 32.92, 64.69, 70.02, 72.64, 125.64, 126.54, 128.09, 144.64, 163.10;

MS (EI) m/z 333 ([M]$^+$, 26), 278 (100), 277 (100), 276 (100), 274 (17);

HRMS (EI) m/z calcd. for C$_{19}$H$_{31}$NO$_2$Si, 333.2124; found 333.2105;

$[\alpha]^{25}_{589}$-37.7 (c 1.1, CH$_2$Cl$_2$).

Example 31

(S)-4-Isopropyl-2-[p-(methoxyethoxymethoxy)phenyl]oxazoline

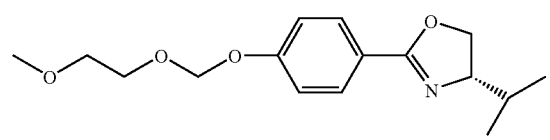

State: colorless oil

IR (neat NaCl, v/cm$^{-1}$) 1667, 1604, 1495, 1454, 1078, 753, 699;

$^1$H NMR (300 MHz, CDCl$_3$, 35° C.) δ 0.92 (d, J=6.9 Hz, 3H, CH(CH$_3$)$_2$), 1.02 (d, J=6.9 Hz, 3H, CH(CH$_3$)$_2$), 1.8-1.9 (m, 1H, CH(CH$_3$)$_2$), 3.35 (s, 1H, CH$_3$O(CH$_2$)$_2$OCH$_2$O), 3.5 (m, 2H, CH$_3$O(CH$_2$)$_2$OCH$_2$O), 3.8 (m, 2H, CH$_3$O(CH$_2$)$_2$OCH$_2$O), 4.0-4.1 (m, 2H, NCHCH$_2$), 4.3-4.4 (m, 1H, NCHCH$_2$), 5.28 (s, 2H, CH$_3$O(CH$_2$)$_2$OCH$_2$O), 7.05 (d, J=9.0 Hz, 2H, Ar), 7.88 (d, J=9.0 Hz, 2H, Ar);

$^{13}$C NMR (75 MHz, CDCl$_3$, 35° C.) δ 18.41, 19.26, 33.17, 59.21, 68.09, 70.24, 71.83, 72.86, 93.47, 115.96, 121.82, 130.02, 159.70, 163.05;

MS (EI) m/z 293 ([M]$^+$, 24), 276 (40), 251 (52), 250 (100), 220 (17), 218 (17);

HRMS (EI) m/z calcd. for C$_{16}$H$_{23}$NO$_4$, 293.1627; found 293.1554;

$[\alpha]^{25}_{589}$-44.7 (c 1.1, CH$_2$Cl$_2$).

Example 32

(S)-4-Isopropyl-2-[p-(tert-butyldimethylsilyloxy)phenyl]oxazoline

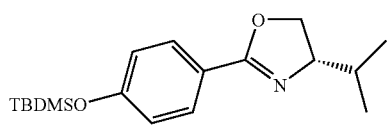

State: colorless oil

IR (neat NaCl, v/cm$^{-1}$) 2957, 2859, 1651, 1606, 1512, 1471, 1354, 1268, 1164, 1074, 913, 839, 806, 782, 673;

$^1$H NMR (300 MHz, CDCl$_3$, 35° C.) δ 0.20 (s, 6H, $^t$BuMe$_2$Si), 1.03 (d, J=6.6 Hz, 3H, CH(CH$_3$)$_2$), 1.05 (s, 9H, $^t$BuMe$_2$Si), 1.30 (d, J=6.6 Hz, 3H, CH(CH$_3$)$_2$), 1.9-2.0 (m, 1H, CH(CH$_3$)$_2$), 4.1-4.2 (m, 2H, NCHCH$_2$), 4.4-4.5 (m, 1H, NCHCH$_2$), 4.87 (s, TBDMSCH$_2$), 7.45 (d, J=8.1 Hz, 2H, Ar), 8.02 (d, J=8.1 Hz, 2H, Ar);

$^{13}$C NMR (75 MHz, CDCl$_3$, 35° C.) δ −5.14, 18.17, 18.47, 19.01, 25.99, 32.92, 64.69, 70.02, 72.64, 125.64, 126.54, 128.09, 144.64, 163.10;

MS (EI) m/z 319 ([M]$^+$, 27), 304 (15), 278 (29), 277 (97), 276 (100), 262 (48), 248 (48), 221 (30), 217 (13), 212 (11);

HRMS (EI) m/z calcd. for C$_{18}$H$_{29}$NO$_2$Si, 319.1968; found 319.1953;

$[\alpha]^{25}_{589}$-39.1 (c 1.0, CH$_2$Cl$_2$).

The compounds obtained in Examples 12 to 15 and Example 21 in Table 1 were confirmed by comparison with known physical property data of the respective compounds.

Example 33

Production of Oxazolines

Under an argon atmosphere, a mixture of 3-phenylpropionic acid (3.0 mmol), (L)-valinol (3.6 mmol), Zn$_4$(OCOCF$_3$)$_6$ O (0.15 mmol) and chlorobenzene (5 mL) was heated under reflux for 12 hours. From the resulting solution, the solvent was removed using an evaporator, and the residues were purified by silica gel column chromatography (hexane/ethyl acetate=10/1 (V/V)) to give (S)-4-isopropyl-2-(2-phenylethyl)-1,3-oxazoline in 86% yield.

The analysis data of the resulting compound and the structural formula of the compound identified thereby will be shown below.

Examples 34 to 45

Production of Oxazolines

The reaction was carried out in the same manner as in Example 33 except that a substrate shown in Table 2 below was used in place of 3-phenylpropionic acid in Example 33, and an amino alcohol shown in Table 2 was used in place of (L)-valinol. The yields of the resulting oxazolines are shown in Table 2 below. In Table 2, A represents 3-phenylpropionic acid, and E represents methyl 3-phenylpropionate.

When methyl 3-phenylpropionate was used, the reaction time was 18 hours.

TABLE 2

| Example | Substrate | Amino alcohol | Product | Yield (%) |
|---|---|---|---|---|
| 34 | E | (i-Pr, H₂N, OH) | (phenethyl oxazoline with i-Pr) | 60 |
| 35 | A | (Ph, H₂N, OH) | (phenethyl oxazoline with Ph) | 81 |
| 36 | E | | | 53 |
| 37 | A | (Bn, H₂N, OH) | (phenethyl oxazoline with Bn) | 97 |
| 38 | E | | | 40 |
| 39 | A | (gem-dimethyl amino alcohol) | (4,4-dimethyl phenethyl oxazoline) | 81 |
| 40 | E | | | 97 |
| 41 | A | (cis-1-amino-2-hydroxyindane) | (indano-fused oxazoline) | 99 |
| 42 | E | | | 79 |
| 43 | A | (t-Bu, H₂N, OH) | (phenethyl oxazoline with t-Bu) | Quantitative |
| 44 | E | | | Quantitative |
| 45 | A | (Bn, H₂N, OH, gem-dimethyl) | (4,4-dimethyl-5-Bn phenethyl oxazoline) | 67 |

The analysis data of the resulting compounds and the structural formulae of the compounds identified thereby are shown below.

Examples 33 and 34

(S)-4-Isopropyl-2-(2-phenylethyl) oxazoline

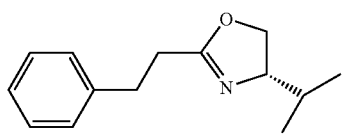

State: colorless oil

IR (neat NaCl, v/cm$^{-1}$) 2958, 1671, 1455, 1365, 1234, 1164, 985, 750, 698;

$^1$H NMR (300 MHz, CDCl$_3$, 35° C.) δ 0.84 (d, J=6.6 Hz, 3H, CH(CH$_3$)$_2$), 0.93 (d, J=6.6 Hz, 3H, CH(CH$_3$)$_2$), 1.69 (sept like, 1H, CH(CH$_3$)$_2$), 2.58 (t, J=7.8 Hz, 2H, CH$_2$CH$_2$), 2.95 (t, J=7.8 Hz, 2H, CH$_2$CH$_2$), 3.89 (m, 2H, CH$_2$O), 4.18 (m, 1H, CHCH$_2$), 7.1-7.3 (m 5H, Ph);

$^{13}$C NMR (75 MHz, CDCl$_3$, 35° C.) δ 18.05, 18.70, 29.80, 32.30, 32.52, 69.77, 72.06, 125.96, 128.11, 128.20, 140.51, 166.23;

MS (EI) m/z (relative intensity) 217 ([M$^+$], 84), 174 (92), 91 (82), 18 (100);

HRMS (EI) m/z calcd. for C$_{14}$H$_{19}$NO, 217.1467; found 217.1460;

$[α]^{25}_{589}$-47.3 (c 1.0, CHCl$_3$).

Examples 35 and 36

(R)-4-Phenyl-2-(2-phenylethyl)oxazoline

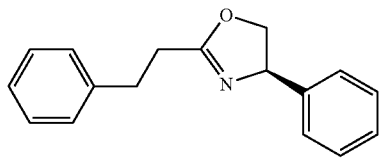

State: colorless oil

IR (neat NaCl, v/cm$^{-1}$) 1667, 1604, 1495, 1454, 1078, 753, 699;

$^1$H NMR (300 MHz, CDCl$_3$, 35° C.) δ 2.71 (t, J=7.5 Hz, 2H, PhCH$_2$CH$_2$), 3.03 (t, J=7.5 Hz, 2H, PhCH$_2$CH$_2$), 4.02 (dd, J=8.4, 8.4 Hz, 1H, NCHCH$_2$), 4.56 (dd, J=8.4, 10.2 Hz, 1H, NCHCH$_2$), 5.13 (m, 1H, NCHCH$_2$), 7.1-7.3 (m 10H, Ph);

$^{13}$C NMR (75 MHz, CDCl$_3$, 35° C.) δ 29.72, 32.15, 69.58, 74.54, 126.10, 126.40, 127.27, 128.24, 128.34, 128.47, 140.36, 142.22, 167.71;

MS (EI) m/z (relative intensity) 251 ([M$^+$], 88), 250 (41), 220 (10), 204 (12), 203 (100), 202 (56), 188 (25), 174 (11), 212 (20);

HRMS (EI) m/z calcd. for C$_{17}$H$_{17}$NO, 251.1310; found 251.1305;

$[α]^{25}_{589}$-47.8 (c 1.0, CHCl$_3$).

Examples 37 and 38

(S)-4-Benzyl-2-(2-phenylethyl)oxazoline

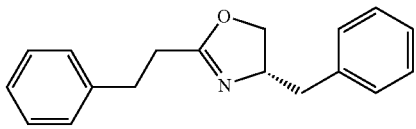

State: colorless oil

IR (neat NaCl, v/cm$^{-1}$) 1667, 1496, 1454, 983, 751, 699;

$^1$H NMR (300 MHz, CDCl$_3$, 35° C.) δ 2.5-2.6 (m, 3H, PhCH$_2$, PhCH$_2$CH$_2$), 2.93 (t, J=8.0 Hz, 2H, PhCH$_2$CH$_2$), 3.00 (dd, J=5.1, 13.8 Hz, 1H, PhCH$_2$), 3.89 (dd, J=7.5, 8.4 Hz, 1H, NCHCH$_2$), 4.09 (dd, J=8.4, 8.4 Hz, 1H, NCHCH$_2$), 4.2-4.4 (m, 1H, NCHCH$_2$), 7.1-7.3 (m 10H, Ph);

$^{13}$C NMR (75 MHz, CDCl$_3$, 35° C.) δ 29.63, 32.03, 41.67, 67.08, 71.37, 125.92, 126.15, 128.02, 128.15, 128.16, 128.94, 137.67, 140.36, 166.75;

MS (EI) m/z (relative intensity) 266 ([M$^+$+H], 19), 265 (100), 244 (13), 236 (23), 224 (10), 217 (26), 212 (20);

HRMS (EI) m/z calcd. for C$_{12}$H$_{21}$NO, 265.1467; found 265.1483;

$[α]^{25}_{589}$-40.9 (c 1.0, CHCl$_3$).

Examples 39 and 40

4,4-Dimethyl-2-(2-phenylethyl)oxazoline

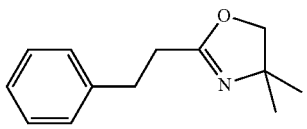

State: colorless oil

IR (neat NaCl, v/cm$^{-1}$) 1668, 16.4, 1496, 1455, 1363, 1146, 1078, 990, 750, 699;

$^1$H NMR (300 MHz, CDCl$_3$, 35° C.) δ 1.23 (s, 6H, NC(CH$_3$)$_2$), 2.55 (t, J=7.5 Hz, 2H, PhCH$_2$CH$_2$), 3.03 (t, J=7.5 Hz, 2H, PhCH$_2$CH$_2$), 3.88 (s, 2H, NCCH$_2$), 7.2-7.3 (m 5H, Ph);

$^{13}$C NMR (75 MHz, CDCl$_3$, 35° C.) δ 28.43, 29.93, 32.29, 66.93, 48.95, 126.04, 128.20, 128.26, 140.50, 164.92;

MS (EI) m/z (relative intensity) 203 ([M$^+$], 100), 202 (65), 188 (22), 162 (16);

HRMS (EI) m/z calcd. for C$_{13}$H$_{17}$NO, 203.1310; found 203.1283;

$[α]^{25}_{589}$-47.3 (c 1.0, CHCl$_3$).

Examples 41 and 42

(3aS,8aR)-2-(2-Phenylethyl)-8, 8a-dihydro-3aH-indeno[1,2-d]oxazole

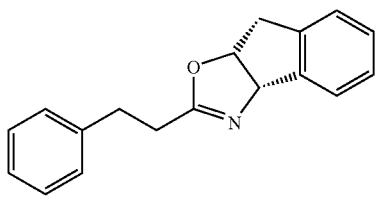

State: white solid

Melting point: 78 to 81° C.;

IR (neat NaCl, v/cm$^{-1}$) 1667, 1604, 1495, 1454, 1078, 753, 699;

$^1$H NMR (300 MHz, CDCl$_3$, 35° C.) δ 2.53 (t, J=7.5 Hz, 2H, PhCH$_2$CH$_2$), 2.90 (t, J=7.5 Hz, 2H, PhCH$_2$CH$_2$), 3.17 (dd, J=1.5, 17.7 Hz, 1H, NCHCHO), 3.38 (dd, J=7.2 17.7 Hz, 1H, NCHCHO), 5.26 (ddd, J=3.0, 7.2, 7.5 Hz, 1H, OCHCH$_2$Ar), 5.49 (d, J=7.5 Hz, 1H, OCHCH$_2$Ar), 7.1-7.5 (m, 9H, Ar);

$^{13}$C NMR (75 MHz, CDCl$_3$, 35° C.) δ 30.01, 32.30, 39.83, 76.53, 82.85, 125.12, 125.37, 126.02, 127.32, 128.14, 128.27, 139.55, 140.40, 142.04, 167.12;

MS (EI) m/z 263 ([M]$^+$, 100), 262 (43), 236 (20), 228 (10), 227 (74), 224 (10), 212 (20), 203 (42), 202 (25), 186 (38), 182 (18), 170 (13), 162 (55);

HRMS (EI) m/z calcd. for C$_{18}$H$_{17}$NO, 263.1310; found 263.1297;

$[\alpha]^{25}_{589}$ -157.8° (c 1.0, CH$_2$Cl$_2$).

Examples 43 and 44

(S)-4-tert-Butyl-2-(2-phenylethyl)oxazoline

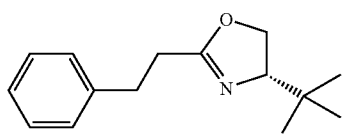

State: white solid

IR (neat NaCl, v/cm$^{-1}$) 2954, 1673, 1362, 1230, 1209, 1171, 983, 698;

$^1$H NMR (300 MHz, CDCl$_3$, 35° C.) δ 0.84 (s, 9H, C(CH$_3$)$_3$), 2.5-2.6 (m, 2H, CH$_2$CH$_2$), 2.94 (t, J=8.1 Hz, 2H, CH$_2$CH$_2$), 3.7-3.8 (m, 1H, NCHCH$_2$), 4.00 (dd, J=8.4, 8.4 Hz, 1H, NCHCH$_2$), 4.11 (dd, J=8.4, 10.2 Hz, 1H, NCHCH$_2$), 7.1-7.3 (m 5H, Ph);

$^{13}$C NMR (75 MHz, CDCl$_3$, 35° C.) δ 25.72, 29.73, 32.30, 33.41, 68.30, 75.70, 125.91, 128.11, 128.15, 140.49, 166.09;

MS (EI) m/z (relative intensity) 231 ([M$^+$], 64), 174 (100), 91 (55);

HRMS (EI) m/z calcd. for C$_{15}$H$_{21}$NO, 231.1623; found 231.1612;

$[\alpha]^{25}_{589}$ -47.1 (c 1.1, CHCl$_3$).

Example 45

(S)-5,5-Dimethyl-2-(2-phenylethyl)-4-benzyloxazoline

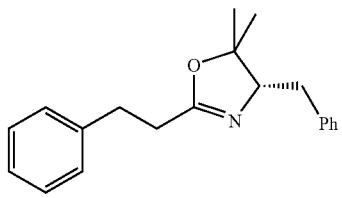

State: colorless oil

IR (neat NaCl, v/cm$^{-1}$) 3027, 2974, 1663, 1496, 1454, 1386, 1370, 1146, 742, 698;

$^1$H NMR (300 MHz, CDCl$_3$, 35° C.) δ 1.22 (s, 3H, CH$_3$), 1.25 (s, 3H, CH$_3$), 2.54 (t, J=8.1 Hz, 2H, PhCH$_2$CH$_2$), 2.66 (dd, 1H, J=7.2, 14.1 Hz, CHCH$_2$Ph), 2.86 (dd, J=7.8, 14.1 Hz, 1H, CHCH$_2$Ph), 2.93 (t, J=8.1 Hz, 1H, PhCH$_2$CH$_2$), 3.92 (dd, J=7.2, 7.8 Hz, 1H, CHCH$_2$Ph), 7.2-7.3 (m, 10H, Ph);

$^{13}$C NMR (75 MHz, CDCl$_3$, 35° C.) δ 21.89, 28.50, 30.20, 32.14, 37.64, 74.72, 85.68, 125.97, 128.16, 128.18, 128.22, 128.81, 139.07, 140.52, 165.16;

MS (EI) m/z 293 ([M]$^+$, 35), 202 (100);

HRMS (EI) m/z calcd. for C$_{20}$H$_{23}$NO, 293.1780; found 293.1791;

$[\alpha]^{25}_{589}$ -99.1 (c 1.1, CH$_2$Cl$_2$).

Examples 46 to 51

Production of Oxazolines

Under an argon atmosphere, a mixture of a dihydrocinnamate (1.0 mmol), L-valinol (1.2 mmol), Zn$_4$(OCOCF$_3$)$_6$O (0.05 mmol) and chlorobenzene (2.5 mL) was heated under reflux for 18 hours. The resulting solution was analyzed by gas chromatography. The yield of each oxazoline is shown in Table 3 below.

TABLE 3

| Example | R | GC yield (%) |
| --- | --- | --- |
| 46 | H | >99 |
| 47 | Me | 94 |
| 48 | Et | 98 |
| 49 | n-Bu | 78 |
| 50 | i-Pr | 75 |
| 51 | PhCH$_2$ | 74 |

Because the same analysis data as in Example 34 was obtained, the compounds obtained in Examples 46 to 51 were identified as (S)-4-isopropyl-2-(2-phenylethyl)-1,3-oxazoline having the following structural formula:

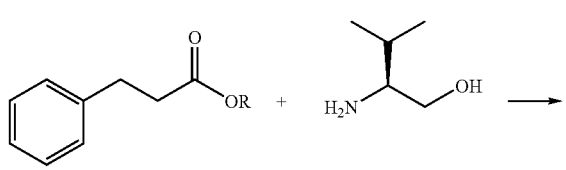

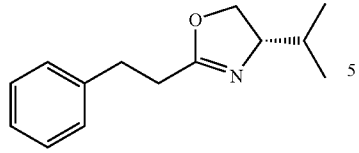

Example 52

Production of Oxazolines

Under an argon atmosphere, a mixture of 4-cyanobenzoic acid (7.2 mmol), L-tert-leucinol (6.0 mmol), $Zn_4(OCOCF_3)_6O$ (0.3 mmol) and chlorobenzene (10 mL) was heated under reflux for 18 hours. From the resulting solution, the solvent was removed using an evaporator, and the residues were purified by silica gel column chromatography (hexane/ethyl acetate=10/1 (V/V)) to give (S)-4-tert-butyl-2-(4-cyanophenyl)-1,3-oxazoline in 78% yield.

In addition, a bisoxazoline, 1,4-bis[(S)-4-t-butyloxazolin-2-yl]benzene was obtained in 19% yield.

The analysis data of the resulting compound and the structural formula of the compound identified thereby are as follows:

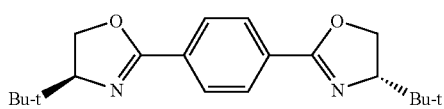

State: white solid

Melting point: 190 to 195° C.;

IR (film NaCl, $v/cm^{-1}$) 2959, 1650, 1356, 1263, 1075, 1054, 968, 904;

$^1$H NMR (300 MHz, $CDCl_3$, 35° C.) δ 0.96 (s, 18H, $C(CH_3)_3$), 4.05 (dd, J=8.1, 10.2 Hz, 1H, $CHCH_2$), 4.24 (dd, J=8.1, 8.1 Hz, 2H, $CHCH_2$), 4.35 (dd, J=8.1, 10.2 Hz, 2H, $CHCH_2$), 7.98 (s, 4H, Ar);

$^{13}$C NMR (75 MHz, $CDCl_3$, 35° C.) δ 25.99, 34.12, 68.83, 76.41, 128.02, 131.88, 130.31, 162.52;

MS (EI) m/z (relative intensity) 328 ([M]$^+$, 1), 313 (4), 271 (100);

HRMS (EI) m/z calcd. for $C_{20}H_{28}N_2O_2$, 328.2151; found 328.2144;

$[\alpha]^{25}_{589}$-98.3 (c 0.27, $CH_2Cl_2$).

Example 53

Production of Oxazolines (S)-4-tert-Butyl-2-(3-cyanophenyl)-1,3-oxazoline was obtained in 78% yield in the same manner as in Example 52 except that 3-cyanobenzoic acid was used in place of 4-cyanobenzoic acid.

The analysis data of the resulting compound and the structural formula of the compound identified therefrom are as follows:

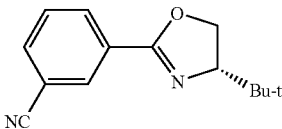

State: white solid

Melting point: 65 to 67° C.;

IR (film NaCl, $v/cm^{-1}$) 2234, 1653, 1361, 1180, 1079, 962, 815, 698;

$^1$H NMR (300 MHz, $CDCl_3$, 35° C.) δ 0.96 (s, 9H, $C(CH_3)_3$), 4.07 (dd, J=8.1, 10.2 Hz, 1H, $NCHCH_2$), 4.26 (dd, J=8.1, 8.7 Hz, 1H, $NCHCH_2$), 4.38 (dd, J=8.7, 10.2 Hz, 1H, $NCHCH_2$), 7.51 (dd, J=6.3, 7.5 Hz, 1H, Ar-5), 7.73 (dd, J=1.5, 7.5 Hz, 1H, Ar-4 or 6), 8.18 (dd, J=1.5, 6.3 Hz, 1H, Ar-4 or 6), 8.25 (dd, J=1.5, 1.5 Hz, Ar-2);

$^{13}$C NMR (75 MHz, $CDCl_3$, 35° C.) δ 25.89, 34.02, 69.16, 76.39, 112.65, 117.97, 129.01, 129.31, 131.75, 132.13, 134, 01, 161.07;

MS (EI) m/z (relative intensity) 228 ([M+H]$^+$, 5), 172 (100), 143 (20), 130 (35);

HRMS (EI) m/z calcd. for $C_{14}H_{16}N_2O$, 228.1263; found 228.1241;

$[\alpha]^{25}_{589}$-59.5 (c 1.0, $CH_2Cl_2$).

Example 54

Production of Oxazolines

Methyl 4-{(S)-4-tert-butyloxazolin-2-yl}benzoate was obtained in 90% yield in the same manner as in Example 52 except that monomethyl terephthalate was used in place of 4-cyanobenzoic acid.

The analysis data of the resulting compound and the structural formula of the compound identified therefrom are as follows:

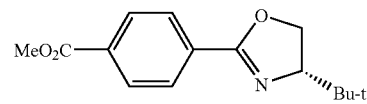

State: white solid

Melting point: 117 to 118° C.;

IR (film NaCl, $v/cm^{-1}$) 1720, 1651, 1434, 1407, 1279, 1105, 1079, 1058, 1014, 972, 866, 708;

$^1$H NMR (300 MHz, $CDCl_3$, 35° C.) δ 0.96 (s, 9H, $C(CH_3)_3$), 3.93 (s, 3H, $COOCH_3$), 4.07 (dd, J=9.0, 10.2 Hz, 1H, $NCHCH_2$), 4.25 (dd, J=9.0, 9.0 Hz, 1H, $NCHCH_2$), 4.37 (dd, J=9.0, 10.2 Hz, 1H, $NCHCH_2$), 8.01 (d, J=8.4 Hz, 2H, Ar), 8.06 (d, J=8.4 Hz, 1H, Ar);

$^{13}$CNMR (75 MHz, $CDCl_3$, 35° C.) δ 25.98, 34.12, 52.26, 68.96, 76.47, 128.13, 129.35, 132.00, 132. 24, 162.30, 166.35;

MS (EI) m/z (relative intensity) 266 ([M+H]$^+$, 19), 265 (100), 244 (13), 236 (23), 224 (10), 217 (26), 212 (20);

HRMS (EI) m/z calcd. for $C_{15}H_{19}NO_3$, 261.1365; found 261.1350;

$[\alpha]^{25}_{589}$-48.9 (c 1.0, $CH_2Cl_2$).

Example 55

Production of Bisoxazolines

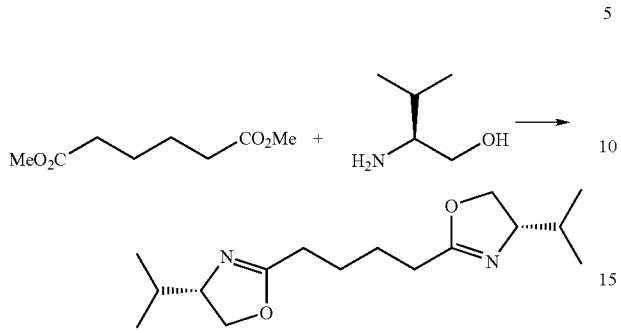

Under an argon atmosphere, a mixture of dimethyl adipate (3 mmol), (L)-valinol (7.2 mmol), $Zn_4(OCOCF_3)_6O$ (0.3 mmol) and chlorobenzene (5 mL) was refluxed for 6 hours, then concentrated, and purified by silica gel column chromatography to give 1,4-bis((S)-4-isopropyl-1,3-oxazolin-2-yl)butane in 64.8% yield.

The resulting compound was identified by comparison with physical property data of the known compound.

Example 56

Production of Unsymmetrical Bisoxazolines

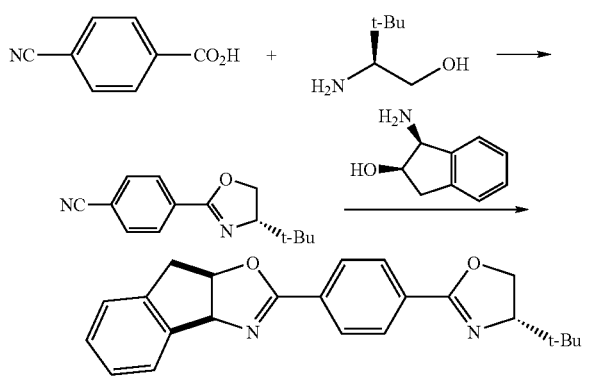

Under an argon atmosphere, a mixture of 4-cyanobenzoic acid (7.2 mmol), L-tert-leucinol (6.0 mmol), $Zn_4(OCOCF_3)_6O$ (0.3 mmol) and chlorobenzene (10 mL) was heated under reflux for 18 hours, then concentrated and purified to give a monooxazoline. Subsequently, the resulting monooxazoline (3.0 mmol), (1S, 2R)-1-aminoindanol (3.6 mmol), $Zn_4(OCOCF_3)_6O$ (0.15 mmol) and chlorobenzene (5 mL) were heated under reflux for 18 hours and then concentrated, and the resulting residues were purified by silica gel column chromatography to give the title compound in 78% yield in the two-step reaction (78% in the first step; >99% in the second step).

The analysis data of the resulting compound, and the structural formula and name of the compound identified thereby, are shown below:

1-{(3aS,8aR)-8, 8a-Dihydro-3aH-indeno [1,2-d]oxazol-2-yl}-4-{(S)-4-tert-butyloxazolin-2-yl}benzene

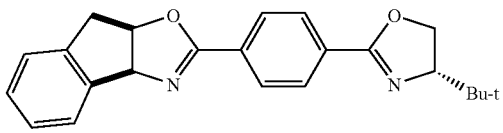

State: white solid

Melting point: 178 to 179° C. (dec.);

IR (film NaCl, $v/cm^{-1}$) 2956, 1644, 1412, 1355, 1086, 1071, 860, 751, 688;

$^1$H NMR (300 MHz, $CDCl_3$, 35° C.) δ 0.95 (s, 9H, $C(CH_3)_3$), 3.36 (dd, J=1.8, 18.0 Hz, 1H, $CH_2Ar$), 3.51 (dd, J=6.6, 18.0 Hz, 1H, $CH_2Ar$), 4.04 (dd, J=8.1, 10.2 Hz, 1H, $CHCH_2$), 4.22 (dd, J=8.1, 1H, $CHCH_2$), 4.34 (dd, J=8.1, 10.2 Hz, 1H, $CHCH_2$), 5.49 (ddd, J=1.8, 6.6, 7.8 Hz, 1H, NCH-CHO), 5.75 (d, J=7.8 Hz, 1H, NCHCHO), 7.25-7.27 (m, 3H, Ar), 7.55-7.58 (m, 1H, Ar), 7.95 (s, 4H, Ar);

$^{13}$C NMR (75 MHz, $CDCl_3$, 35° C.) δ 25.99, 34.11, 39.90, 68.84, 76.42, 77.18, 125.21, 125.56, 127.42, 128.01, 128.15, 128.44, 130.21, 130.42, 139.60, 141.74, 162.47, 163.28;

MS (EI) m/z (relative intensity) 360 ([M]$^+$, 1), 345 (1), 303 (45), 227 (16);

HRMS (EI) m/z calcd. for $C_{23}H_{24}N_2O_2$, 360.1838; found 360.1843;

$[α]^{25}_{589}$-140.6 (c 1.0, $CH_2Cl_2$).

Example 57

Production of Unsymmetrical Bisoxazolines

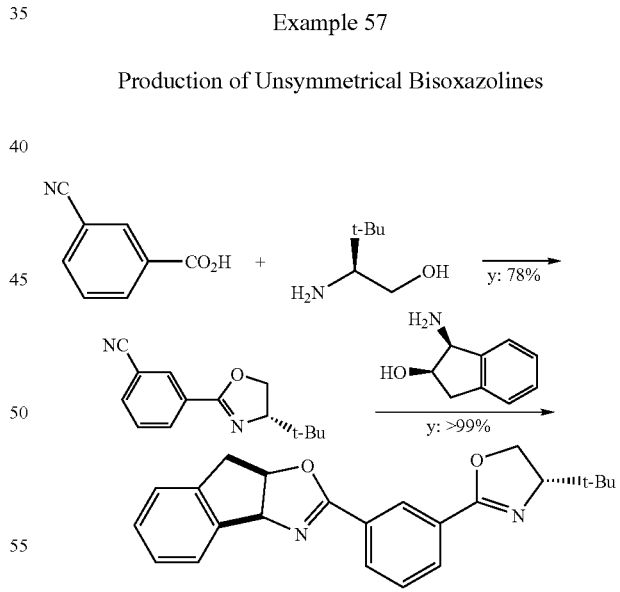

The reaction was carried out in the same manner as in Example 56 except that 3-cyanobenzoic acid was used, whereby as shown in the scheme, 1,3-di-substituted unsymmetrical bisoxazoline was obtained in 78% yield in the two-step reaction (78% in the first step; >99% in the second step).

The analysis data of the resulting compound, and the structural formula and name of the compound identified thereby, are shown below:

1-{(3aS,8aR)-8,8a-dihydro-3aH-indeno [1,2-d]oxazol-2-yl}-3-{(S)-4-tert-butyloxazolin-2-yl}benzene

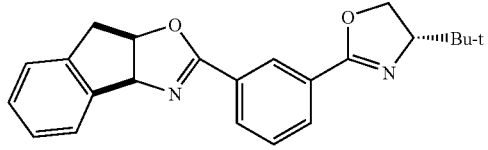

State: white solid

¹H NMR (300 MHz, CDCl₃, 35° C.) δ 0.94 (s, 9H, C(CH₃)₃), 3.36 (dd, J=1.8, 18.0 Hz, 1H, OCHCH₂Ar), 3.49 (dd, J=6.6, 18.0 Hz, 1H,), 4.02 (dd, J=7.5, 10.2 Hz, 1H, NCHCH₂), 4.24 (dd, J=7.5, 9.0 Hz, 1H, NCHCH₂), 4.32 (dd, J=9.0, 10.2 Hz, 1H, NCHCH₂), 5.47 (ddd, J=1.8, 6.6, 7.5 Hz, 1H, NCHCHO), 5.73 (d, J=7.5 Hz, 1H, NCHCHO), 7.2-7.3 (m, 3H, Ar), 7.5-7.6 (m, 1H, Ar), 8.0-8.1 (m, 2H, Ar), 8.47 (dd, J=1.5, 1.5 Hz, Ar-2);

¹³C NMR (75 MHz, CDCl₃, 35° C.) δ 25.93, 34.04, 39.79, 68.77, 76.33, 77.05, 83.33, 125.14, 125.51, 127.33, 128.02, 128.09, 1228.15, 128.34, 130.75, 130.82, 139.52, 141.77, 162.35, 163.22.

Example 58

Production of Amides

Under an argon atmosphere, a mixture of methyl benzoate (3.0 mmol), 2-aminoethanol (3.6 mmol), Zn₄(OCOCF₃)₆O (0.15 mmol) and methylene chloride (2.5 mL) was stirred at room temperature for 3 days, and as a result, N-(2-hydroxyethyl)benzamide was obtained in 11% yield. The resulting compound was identified by comparison with physical property data of the known compound.

Example 59

Production of Amides

Under an argon atmosphere, a mixture of methyl phenylpropionate (3.0 mmol), benzylamine (3.6 mmol), Zn₄(OCOCF₃)₆O (0.15 mmol) and methylene chloride (5 mL) was heated under reflux for 18 hours, and as a result, N-benzyl-3-phenylpropanamide was obtained in 21% yield. The resulting compound was identified by comparison with physical property data of the known compound.

Example 60

Production of Amides

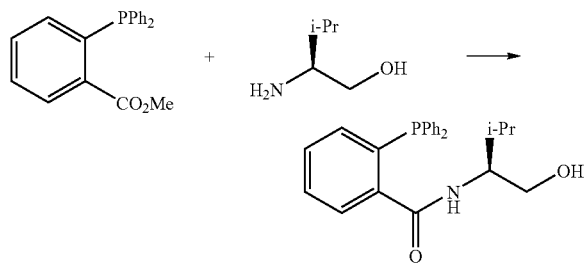

Under an argon atmosphere, a mixture of methyl 2-(diphenylphosphino)benzoate (3.0 mmol), (L)-valinol (3.6 mmol), Zn₄(OCOCF₃)₆O (0.15 mmol) and methylene chloride (5 mL) was heated under reflux for 12 hours, and as a result, the corresponding amide was obtained in 90% yield. The resulting compound was identified by comparison with physical property data of the known compound.

Example 61

Production of Oxazolines

Under an argon atmosphere, a mixture of γ-butyrolactone (3.0 mmol), (L)-valinol (3.6 mmol), Zn₄(OCOCF₃)₆O (0.15 mmol) and chlorobenzene (5 mL) was heated under reflux for 18 hours. After the solvent was removed, the residues were purified by silica gel column chromatography to give (S)-2-(3-hydroxypropyl)-4-isopropyloxazoline in 68% yield.

The analysis data of the resulting compound and the structural formula of the compound identified thereby are shown below:

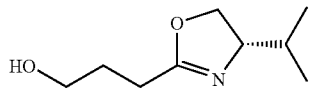

State: colorless oil

IR (neat NaCl, v/cm⁻¹) 3298, 2960, 1664, 1468, 1368, 984;

¹H NMR (300 MHz, CDCl₃, 35° C.) δ 0.88 (d, J=6.9 Hz, 3H, CH(CH₃)₂), 0.95 (d, J=6.9 Hz, 3H, CH(CH₃)₂), 1.6-1.8 (m, 1H, CH(CH₃)₂), 1.89 (tt, J=6.0, 6.6 Hz, 2H, HOCH₂CH₂CH₂), 2.42 (t, J=6.6 Hz, 2H, HOCH₂CH₂CH₂), 3.69 (t, J=6.0 Hz, 2H, HOCH₂CH₂CH₂), 3.8-4.0 (m, 2H, NCHCH₂), 4.2-4.3 (m, 1H, NCHCH₂), 4.4 (br, 1H, OH);

¹³C NMR (75 MHz, CDCl₃, 35° C.) δ 18.23, 18.67, 26.02, 28.51, 32.62, 62.25, 70.38, 71.71, 168.29.

MS (EI) m/z 128 ([M-i-Pr]⁺, 95), 110 (100);

HRMS (EI) m/z calcd. for C₉H₁₆NO₂, ([M−H]+), 170.1181; found 170.1207;

[α]²⁵₅₈₉ −49.5 (c 1.0, CH₂Cl₂).

Examples 62 to 64

Production of Oxazolines

The same operation as in Example 61 was carried out except that lactones shown in Table 4 were used as the lactone substrate in Example 62. The results are shown in Table 4. However, the reaction time in Example 64 was 36 hours.

TABLE 4

| Example | Lactone | Product | Yield (%) |
|---------|---------|---------|-----------|
| 62 | (δ-valerolactone) | HO-(CH2)4-oxazoline-iPr | 85 |
| 63 | (ε-caprolactone) | HO-(CH2)5-oxazoline-iPr | >99 |
| 64 | (γ-ethyl-γ-butyrolactone) | HO-CH(Et)-CH2CH2-oxazoline-iPr | 52 |

The analysis data of the resulting compounds, and the structural formulae and names of the compounds identified thereby, are shown below:

Example 62

(S)-2-(4-Hydroxybutyl)-4-isopropyloxazoline

State: colorless oil

IR (neat NaCl, v/cm$^{-1}$) 3299, 2959, 2873, 1662, 1542, 1464, 1368, 1066, 984;

$^1$H NMR (300 MHz, CDCl$_3$, 35° C.) δ 0.87 (d, J=6.9 Hz, 3H, CH(CH$_3$)$_2$), 0.95 (d, J=6.9 Hz, 3H, CH(CH$_3$)$_2$), 1.5-1.8 (m, 5H, CH$_2$CH$_2$CH$_2$OH and CH(CH$_3$)$_2$), 2.31 (t, J=7.2 Hz, 2H, CH$_2$(CH$_2$)$_3$OH), 3.60 (t, J=6.0 Hz, 2H, CH$_2$OH), 3.8-3.9 (m, 2H, NCHCH$_2$), 4.0 (br, 1H, OH), 4.1-4.3 (m, 1H, NCHCH$_2$);

$^{13}$C NMR (75 MHz, CDCl$_3$, 35° C.) δ 17.85, 18.51, 21.96, 27.38, 32.01, 32.30, 61.07, 69.65, 71.51, 167.68;

MS (EI) m/z 185 ([M]$^+$, 100), 170 (11), 168 (19), 156(63);

HRMS (EI) m/z calcd. for C$_{10}$H$_{19}$NO$_2$, 185.1416; found 185.1411;

[α]$^{25}_{589}$-43.3 (c 1.2, CH$_2$Cl$_2$).

Example 63

(S)-2-(5-Hydroxypentyl)-4-isopropyloxazoline colorless oil;

IR (neat NaCl, v/cm$^{-1}$) 3309, 2934, 2871, 1664, 1465, 1368, 984;

$^1$H NMR (300 MHz, CDCl$_3$, 35° C.) δ 0.87 (d, J=6.9 Hz, 3H, CH(CH$_3$)$_2$), 0.94 (d, J=6.9 Hz, 3H, CH(CH$_3$)$_2$), 1.3-1.8 (m, 7H, (CH$_2$)$_3$CH$_2$OH and CH(CH$_3$)$_2$), 2.28 (t, J=7.5 Hz, 2H, CH$_2$(CH$_2$)$_3$OH), 3.5 (br, 1H, OH), 3.60 (t, J=6.3 Hz, 2H, CH$_2$OH), 3.8-3.9 (m, 2H, NCHCH$_2$), 4.1-4.3 (m, 1H, NCHCH$_2$);

$^{13}$C NMR (75 MHz, CDCl$_3$, 35° C.) δ 17.79, 18.54, 25.26, 25.53, 27.80, 32.08, 32.29, 61.77, 69.54, 71.54, 167.48;

MS (EI) m/z 199 ([M]$^+$, 28), 184 (10), 182 (36), 170 (20), 169 (27), 158 (36), 157 (100);

HRMS (EI) m/z calcd. for C$_{11}$H$_{21}$NO$_2$, 199.1572; found 199.1543;

[α]$^{25}_{589}$-46.0 (c 1.2, CH$_2$Cl$_2$).

Example 64

(4S)-2-(3-Hydroxypentyl)-4-isopropyloxazoline

State: colorless oil

IR (neat NaCl, v/cm$^{-1}$) 3316, 2961, 1668, 1465, 1364, 987;

$^1$H NMR (300 MHz, CDCl$_3$, 35° C.) δ 0.87 (d, J=6.9 Hz, 3H, CH(CH$_3$)$_2$), 0.95 (t, J=6.9 Hz, 3H, CH$_2$CH$_3$), 1.4-1.6 (m, 2H, CH$_2$CH$_3$), 4.7-4.9 (m, 3H, HOCH(Et)CH$_2$CH$_2$, CH(CH$_3$)$_2$), 2.3-2.5 (m, 2H, HOCH(Et)CH$_2$CH$_2$), 3.5-3.6 (m, 1H, HOCH(Et)CH$_2$CH$_2$), 3.8-4.0 (m, 2H, NCHCH$_2$), 4.2-4.3 (m, 1H, NCHCH$_2$), 4.4 (br, 1H, OH);

$^{13}$C NMR (75 MHz, CDCl$_3$, 35° C.) δ 10.03, 10.10, 18.29, 18.31, 18.73, 18.79, 25.34, 25.39, 30.44, 32.35, 32.50, 32.67, 70.32, 70.38, 71.77, 71.85, 72.78, 72.86, 168.36, 168.47;

MS (EI) m/z 198 ([M−H]+, 33), 182 (14), 179 (20), 167 (29), 165 (58), 153 (94);

HRMS (EI) m/z calcd. for C$_{11}$H$_{20}$NO$_2$, ([M−H]$^+$), 198.1494; found 198.1515.

Example 65

Production of Peptides by Condensation of β-Amino Acid

Under an argon atmosphere, a mixture of Zn$_4$(OAc)$_6$O (0.25 mmol) and methyl 3-aminobutyrate (5.0 mmol) was stirred at 130° C. for 6 hours. When the resulting product was analyzed with a liquid chromatograph mass spectrometer, it was confirmed that the inversion rate of methyl 3-anubibytrate was 100% and dimer/trimer had been formed in the ratio of 75/25.

Example 66

Synthesis of Oxazolines

Under an argon atmosphere, a mixture of benzyl 3-phenylpropionate (1.5 mmol), (L)-valinol (1.8 mmol), Zn$_4$(OCOCF$_3$)$_6$O (0.15 mmol) and chlorobenzene (2.5 mL) was heated under reflux for 18 hours. From the resulting solution, the solvent was removed using an evaporator, and the residues were purified by silica gel column chromatography to give (S)-4-isopropyl-2-(2-phenylethyl)-1,3-oxazoline in 74% yield. The compound was identified by comparison with physical property data of the known compound.

Example 67

Production of Oxazolines

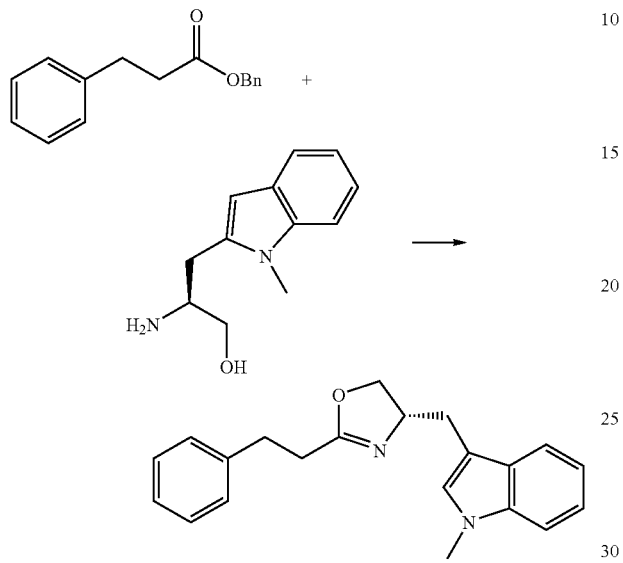

Under an argon atmosphere, a mixture of benzyl 3-phenylpropionate (1.5 mmol), (S)-2-(N-methylindol-3-ylmethyl)-2-aminoethanol (1.5 mmol), Zn$_4$(OCOCF$_3$)$_6$O (0.15 mmol) and chlorobenzene (2.5 mL) was heated under reflux for 18 hours. From the resulting solution, the solvent was removed using an evaporator, and the residues were purified by silica gel column chromatography to give (S)-4-(N-methylindol-3-ylmethyl)-2-(2-phenylethyl)-1,3-oxazoline in 76% yield. The compound was identified by comparison with physical property data of the known compound.

Example 68

Production of Oxazolines

Under an argon atmosphere, a mixture of methyl 4-hydroxymethylbenzoate (1.5 mmol), (L)-valinol (1.8 mmol), Zn$_4$(OCOCF$_3$)$_6$O (0.15 mmol) and chlorobenzene (2.5 mL) was heated under reflux for 12 hours. From the resulting solution, the solvent was removed using an evaporator, and the residues were purified by silica gel column chromatography to give (S)-4-isopropyl-2-(4-hydroxymethylphenyl)-1,3-oxazoline in 66% yield. The compound was identified by comparison with physical property data of the known compound.

Example 69

Production of Oxazolines

Under an argon atmosphere, a mixture of methyl 4-hydroxybenzoate (1.5 mmol), (L)-valinol (1.8 mmol), Zn$_4$(OCOCF$_3$)$_6$O (0.15 mmol) and chlorobenzene (2.5 mL) was heated under reflux for 12 hours. From the resulting solution, the solvent was removed using an evaporator, and the residues were purified by silica gel column chromatography to give (S)-4-isopropyl-2-(4-hydroxyphenyl)-1,3-oxazoline in 58% yield. The compound was identified by comparison with physical property data of the known compound.

INDUSTRIAL APPLICABILITY

According to the present invention, there can be provided a method for producing an azoline compound highly selectively and efficiently from an aminochalcogenide, a carboxylic acid, a carboxylate and nitriles, and there can be further provided a method for producing an amide compound efficiently from primary amines and a carboxylic acid or a carboxylate and a method for producing peptides efficiently by condensation of amino acids. The azoline obtained in the present invention is useful as a ligand of a metal complex, a pharmaceutical intermediate or the like, and the amide compound and peptides are useful as intermediates of various compounds.

The invention claimed is:

1. A zinc compound represented by the formula (12).

$$Zn_4(OCOCF_3)_6O \qquad (12)$$

2. A method for producing an azoline compound represented by the general formula (3):

wherein R$^1$ represents an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; R$^3$, R$^4$, R$^5$ and R$^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from R$^3$, R$^4$, R$^5$ and R$^6$ may bond to each other to form a ring; and Z$^1$ represents an oxygen atom, a sulfur atom or a selenium atom;

comprising reacting a carboxylic acid or a carboxylic acid derivative represented by the general formula (1):

$$R^1CO_2R^2 \qquad (1)$$

wherein R$^1$ is as defined above; R$^2$ represents a hydrogen atom, an optionally substituted alkyl group or an optionally substituted aryl group; and R$^1$ and R$^2$ may bond to each other to form a ring;

with an aminochalcogenide represented by the general formula (2):

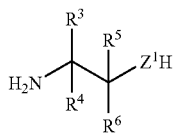

(2)

wherein $R^3$, $R^4$, $R^5$, $R^6$ and $Z^1$ are as defined above;
in the presence of the zinc compound according to claim 1.

3. A method for producing a bisazoline compound represented by the general formula (9):

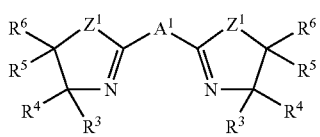

(9)

wherein $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; $Z^1$ represents an oxygen atom, a sulfur atom or a selenium atom; and $A^1$ represents a single bond, a divalent hydrocarbon group or a divalent heterocyclic group;
comprising reacting a compound represented by the general formula (8):

$$R^2OCO\text{-}A^1\text{-}CO_2R^2 \qquad (8)$$

wherein $R^2$ represents a hydrogen atom, an optionally substituted alkyl group or an optionally substituted aryl group; and $A^1$ is as defined above;
with an aminochalcogenide represented by the general formula (2):

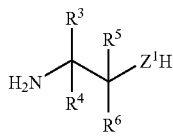

(2)

wherein $R^3$, $R^4$, $R^5$, $R^6$ and $Z^1$ are as defined above;
in the presence of the zinc compound according to claim 1.

4. A method for producing an azoline compound represented by the general formula (5):

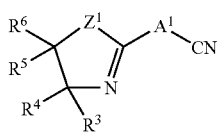

(5)

wherein $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; $A^1$ represents a single bond, a divalent hydrocarbon group or a divalent heterocyclic group ; and $Z^1$ represents an oxygen atom, a sulfur atom or a selenium atom;
comprising reacting cyanocarboxylic acids represented by the general formula (8-2):

$$NC\text{-}A^1\text{-}CO_2R^2 \qquad (8\text{-}2)$$

wherein $R^2$ represents a hydrogen atom, an optionally substituted alkyl group or an optionally substituted aryl group; and $A^1$ is as defined above;
with an aminochalcogenide represented by the general formula (2):

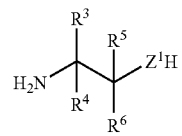

(2)

wherein $R^3$, $R^4$, $R^5$, $R^6$ and $Z^1$ are as defined above;
in the presence of the zinc compound according to claim 1.

5. A method for producing an unsymmetrical bisazoline compound represented by the general formula (9-2):

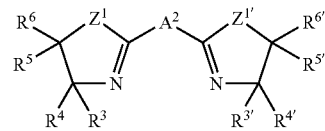

(9-2)

wherein $R^3$, $R^4$, $R^5$ and $R^6$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^3$, $R^4$, $R^5$ and $R^6$ may bond to each other to form a ring; $R^{3'}$, $R^{4'}$, $R^{5'}$ and $R^{6'}$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; two arbitrary groups selected from $R^{3'}$, $R^{4'}$, $R^{5'}$ and $R^{6'}$ may bond to each other to form a ring; $A^2$ represents a single bond, a divalent hydrocarbon group or a divalent heterocyclic group; Z represents an oxygen atom, a sulfur atom or a selenium atom; and
$Z^{1'}$ represents an oxygen atom, a sulfur atom or a selenium atom;
comprising reacting a compound represented by the general formula (8-3):

$$R^2OCO\text{-}A^2\text{-}X^1 \qquad (8\text{-}3)$$

wherein $R^2$ represents a hydrogen atom, an optionally substituted alkyl group or an optionally substituted aryl group; $A^2$ is as defined above; and $X^1$ represents a cyano group or a carboxyl group;

with an aminochalcogenide represented by the general formula (2):

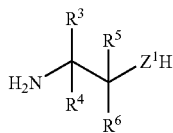

(2)

wherein $R^3$, $R^4$, $R^5$, $R^6$ and $Z^1$ are as defined above;
in the presence of the zinc compound according to claim 1; and reacting the reaction product with an aminochalcogenide represented by the general formula (2-2):

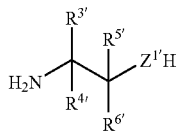

(2-2)

wherein $R^{3'}$, $R^{4'}$, $R^{5'}$, $R^{6'}$ and $Z^{1'}$ are as defined above.

6. A method for producing amides represented by the general formula (7):

$R^1CONHR^8$ (7)

wherein $R^1$ represents an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; and $R^8$ represents an optionally substituted hydrocarbon group;

comprising reacting a carboxylic acid or a carboxylic acid derivative represented by the general formula (1):

$R^1CO_2R^2$ (1)

wherein $R^1$ is as defined above; $R^2$ represents a hydrogen atom, an optionally substituted alkyl group or an optionally substituted aryl group; and $R^1$ and $R^2$ may bond to each other to form a ring;

with amines represented by the general formula (6):

$R^8NH_2$ (6)

wherein $R^8$ is as defined above;
in the presence of the zinc compound according to claim 1.

7. A method for producing bisamides represented by the general formula (7-2):

$R^8NHCO-A^3-CONHR^8$ (7-2)

wherein $R^8$ represents an optionally substituted hydrocarbon group; and $A^3$ represents a single bond, a divalent hydrocarbon group or a divalent heterocyclic group;

comprising reacting a dicarboxylic acid represented by the general formula (8-4):

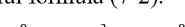

$R^2OCO-A^3-CO_2R^{2'}$ (8-4)

wherein $R^2$ and $R^{2'}$ may be the same or different and each represents a hydrogen atom, an optionally substituted alkyl group or an optionally substituted aryl group; and $A^3$ is as defined above;

with amines represented by the general formula (6):

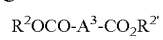

$R^8NH_2$ (6)

wherein $R^8$ is as defined above;
in the presence of the zinc compound according to claim 1.

8. A method for producing cyanoamides represented by the general formula (7-3):

$R^8NHCO-A^2-CN$ (7-3)

wherein $R^8$ represents an optionally substituted hydrocarbon group; and $A^2$ represents a single bond, a divalent hydrocarbon group or a divalent heterocyclic group;

comprising reacting cyanocarboxylic acids represented by the general formula (8-2):

$NC-A^2-CO_2R^2$ (8-2)

wherein $R^2$ represents a hydrogen atom, an optionally substituted alkyl group or an optionally substituted aryl group; and $A^2$ is as defined above;

with amines represented by the general formula (6):

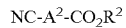

$R^8NH_2$ (6)

wherein $R^8$ is as defined above;
in the presence of the zinc compound according to claim 1.

9. A method for producing peptides represented by the general formula (11):

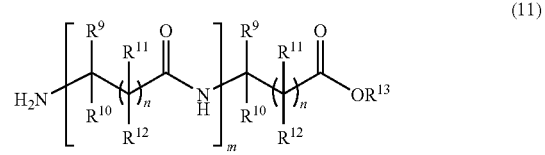

(11)

wherein $R^9$, $R^{10}$, $R^{11}$ and $R^{12}$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; a plurality of $R^9$s, $R^{10}$s, $R^{11}$s or $R^{12}$s may be the same or different; $R^{13}$ represents a hydrogen atom, an optionally substituted alkyl group or an optionally substituted aryl group; n represents an integer; and "m" represents an integer of 1 or more;

comprising subjecting same or different amino acids represented by represented by the general formula (10) to intermolecular condensation with one another:

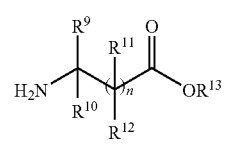

(10)

wherein $R^9$, $R^{10}$, $R^{11}$ and $R^{12}$ may be the same or different and each represents a hydrogen atom, an optionally substituted hydrocarbon group, an optionally substituted alkoxy group, an optionally substituted alkoxycarbonyl group, a halogen atom, a substituted amino group, a substituted carbamoyl group or an optionally substituted heterocyclic group; and $R^{13}$ and n are as defined above;

in the presence of the zinc compound according to claim 1.

* * * * *